US012642713B2

(12) United States Patent
Tang et al.

(10) Patent No.: US 12,642,713 B2
(45) Date of Patent: Jun. 2, 2026

(54) ABSORBENT ARTICLES HAVING AN APERTURED TOPSHEET COMPRISING CELLULOSE-BASED FIBERS

(71) Applicant: The Procter & Gamble Company, Cincinnati, OH (US)

(72) Inventors: Li Tang, Bejing (CN); Xiaoxin Liu, Beijing (CN); Kun Sun, Beijing (CN); Gueltekin Erdem, Beijing (CN); Fancheng Wang, Beijing (CN); Gerard Alain Viens, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 309 days.

(21) Appl. No.: 18/225,874

(22) Filed: Jul. 25, 2023

(65) Prior Publication Data

US 2024/0033138 A1 Feb. 1, 2024

(30) Foreign Application Priority Data

Jul. 29, 2022 (WO) ................ PCT/CN2022/108937

(51) Int. Cl.
*A61F 13/15* (2006.01)
*A61F 13/511* (2006.01)
(Continued)

(52) U.S. Cl.
CPC ...... *A61F 13/5116* (2013.01); *A61F 13/5121* (2013.01); *A61F 2013/530233* (2013.01)

(58) Field of Classification Search
CPC .............. A61F 13/5116; A61F 13/5121; A61F 2013/530233
See application file for complete search history.

(56) References Cited

U.S. PATENT DOCUMENTS

| | | |
|---|---|---|
| 7,569,039 B2 | 8/2009 | Matsuda |
| 7,744,579 B2 | 6/2010 | Langdon et al. |

(Continued)

FOREIGN PATENT DOCUMENTS

| | | |
|---|---|---|
| JP | 4290594 B2 | 4/2009 |
| JP | 5933193 B2 | 5/2016 |

(Continued)

OTHER PUBLICATIONS

PCT Search Report and Opinion for PCT/CN2022/108937 dated Jan. 24, 2023; 12 pages.

(Continued)

*Primary Examiner* — Jacqueline F Stephens
(74) *Attorney, Agent, or Firm* — Anna E. Haller; Angela K. Haughey

(57) ABSTRACT

The present invention relates absorbent article having a wearer facing surface and a garment facing surface, the absorbent article comprising: a topsheet, a backsheet, and a layer of absorbent material disposed between the topsheet and the backsheet, wherein the topsheet comprises a first layer comprising cellulose-based fibers, the first layer comprising a first surface, an opposite second surface, and a plurality of apertures having side walls, wherein the first surface of the first layer forms at least part of the wearer facing surface; wherein the first surface of the first layer comprises at least one non-aperture area having a first non-aperture area contact angle as measured by Contact Angle Test; and wherein each of majority of the apertures has a side wall having an aperture contact angle as measured by Contact Angle Test, the aperture contact angle being higher than the first non-aperture area contact angle.

19 Claims, 10 Drawing Sheets

(51) Int. Cl.
  *A61F 13/512*  (2006.01)
  *A61F 13/53*  (2006.01)

(56)     References Cited

U.S. PATENT DOCUMENTS

| | | | |
|---|---|---|---|
| 8,475,424 B2 | 7/2013 | Fujimoto et al. | |
| 10,568,782 B2 | 2/2020 | Morimoto et al. | |
| 10,624,797 B2 | 4/2020 | Morimoto et al. | |
| 10,624,798 B2 | 4/2020 | Morimoto | |
| 10,624,799 B2 | 4/2020 | Morimoto et al. | |
| 10,632,024 B2 | 4/2020 | Morimoto et al. | |
| 10,632,025 B2 | 4/2020 | Morimoto et al. | |
| 10,744,044 B2 | 8/2020 | Morimoto et al. | |
| 10,786,399 B2 | 9/2020 | Bäck | |
| 10,973,704 B2 | 4/2021 | Morimoto et al. | |
| 11,298,273 B2 | 4/2022 | Morimoto et al. | |
| 11,607,350 B2 | 3/2023 | Morimoto et al. | |
| 11,622,894 B2 | 4/2023 | Morimoto et al. | |
| 11,642,252 B2 | 5/2023 | Morimoto | |
| 11,642,254 B2 | 5/2023 | Morimoto et al. | |
| 2005/0107763 A1 | 5/2005 | Matsuda | |
| 2014/0121625 A1* | 5/2014 | Kirby | A61F 13/51108 604/383 |
| 2018/0161474 A1* | 6/2018 | Klofta | B01J 20/264 |
| 2018/0333310 A1 | 11/2018 | Agami | |
| 2019/0070048 A1 | 3/2019 | Neeb et al. | |
| 2019/0105209 A1* | 4/2019 | Erdem | A61F 13/476 |
| 2019/0117472 A1* | 4/2019 | Erdem | B32B 7/14 |
| 2019/0117473 A1 | 4/2019 | Rosati et al. | |
| 2020/0261282 A1 | 8/2020 | Li et al. | |
| 2023/0225912 A1 | 7/2023 | Morimoto et al. | |
| 2023/0225914 A1 | 7/2023 | Morimoto et al. | |
| 2024/0024169 A1 | 1/2024 | Wang | |

FOREIGN PATENT DOCUMENTS

| | | | |
|---|---|---|---|
| WO | 2006017718 A1 | 2/2006 | |
| WO | 2017173643 A1 | 10/2017 | |

OTHER PUBLICATIONS

All Office Actions; U.S. Appl. No. 18/354,697, filed Jul. 19, 2023.
Unpublished U.S. Appl. No. 18/354,697, filed Jul. 19, 2023, to Fancheng Wang et al.

* cited by examiner

9003

9010          9010

9012

9011

9012

L 9010          9010

W

2013

9001

9002

9007

9002

65°          9009

65°          9003

9005

3700

ABSORBENT ARTICLES HAVING AN APERTURED TOPSHEET COMPRISING CELLULOSE-BASED FIBERS

CROSS-REFERENCE TO RELATED APPLICATIONS

This application claims priority under 35 U.S.C. § 119 to Chinese PCT Patent Application Serial No. PCT/CN2022/108937, filed on Jul. 29, 2022, the entire disclosures of which are hereby incorporated by reference.

FIELD OF THE INVENTION

The present invention relates to an absorbent article comprising an apertured topsheet, the topsheet comprising natural fibers.

BACKGROUND OF THE INVENTION

Absorbent articles have been used as personal hygiene products, such as sanitary napkins, infant disposable diapers, training pants for toddlers, adult incontinence undergarments, and the like. Such absorbent articles are designed to absorb and contain body exudates, in particularly large quantities of urine, runny BM, and/or menses (together the "fluids"). These absorbent articles may comprise several layers providing different functions, for example, a topsheet, a backsheet, and an absorbent core disposed therebetween, among other layers (e.g., acquisition layer, distribution layer, etc.) as desired.

One of design criteria of topsheets in absorbent articles is to reduce the amount of time the fluids spend on the topsheets prior to being absorbed by the absorbent article. If the fluids remain on the surfaces of the topsheets for too long of a period of time, wearers may not feel dry and discomfort may increase. Another desirable quality of topsheets is prevention of fluid flow-back through a topsheet and provision of dryness feel.

To solve the problem of the wearer's skin feeling wet because of prolonged fluid residency on topsheets, apertured topsheets have been used to allow for faster fluid penetration into the absorbent article. Although apertured topsheets have generally reduced fluid pendency on topsheets, it may result in fluid flow-back through a topsheet.

Meanwhile, topsheets acquire and retain some fluid in small capillaries that might exist between fibers which may be visually perceptible to the user of the product as an undesirable stain. It is also a desirable characteristic of absorbent article to present a clean user contacting surface with less stain.

Recently, there has been an increased interest in supplementing or substituting synthetic components of nonwovens with natural fibers or cellulose-based fibers to meet consumers' needs for materials which are natural and gentle to the skin and more environmentally friendly. For example, natural fibers especially natural cellulose-based fibers such as cotton may be mixed with synthetic fibers, or may take the place of synthetic fibers.

Natural fibers tend to be highly hydrophilic after breaching and washing. Therefore, in an absorbent article with a topsheet comprising natural fibers, the body fluids remain on and in the topsheet for a long period of time which results in a wet feel and skin discomfort for the user. As an effort to solve the problem of the skin feeling wet during use, the topsheet comprising natural fibers may be treated with a treatment and/or have a plurality of apertures. Although apertured topsheets have generally reduced fluid pendency on topsheets by enabling faster body fluids penetration, apertured hydrophobic topsheets may nevertheless still have a relatively high run-off, e.g. due to relatively small apertures through which liquid only slowly or even not at all penetrates the topsheets.

There is still a need for an absorbent article with a topsheet comprising cellulosed-based fibers which can reduce fluid flow-back through a topsheet without compromising a fluid acquisition speed.

There is also a continuous need for an absorbent article with a topsheet comprising cellulose-based fibers which can provide improved surface cleanness against body fluid.

SUMMARY OF THE INVENTION

The present invention relates to an absorbent article having a wearer facing surface and a garment facing surface, the absorbent article comprising: a topsheet, a backsheet, and a layer of absorbent material disposed between the topsheet and the backsheet, wherein the topsheet comprises a first layer comprising cellulose-based fibers, the first layer comprising a first surface, an opposite second surface, and a plurality of apertures having side walls, wherein the first surface of the first layer forms at least part of the wearer facing surface; wherein the first surface of the first layer comprises at least one non-aperture area having a first non-aperture area contact angle as measured by Contact Angle Test; and wherein each of majority of the apertures has a side wall having an aperture contact angle as measured by Contact Angle Test, the aperture contact angle being higher than the first non-aperture area contact angle.

The present invention also relates to a method for producing an apertured nonwoven comprising steps of: a) providing a first layer comprising cellulose-based fibers, a first surface and an opposite second surface, b) providing an aperturing apparatus comprising a first forming member and a second forming member which engages the first forming member, wherein the first forming member comprises a plurality of pins on its surface and the second forming member comprises a plurality of recesses on its surface, c) wetting the pins on the first forming member with a treatment having a HLB value not higher than about 13, and d) moving the first layer between the first and second forming members so that apertures are formed in the first layer as the pins on the first forming member and the recesses on the second forming member are engaged, wherein the first surface of the first layer comprises at least one non-aperture area having a first non-aperture area contact angle measured by Contact Angle Test, and wherein each of majority of the apertures has a side wall having an aperture contact angle as measured by Contact Angle Test, the aperture contact angle being higher than the first non-aperture area contact angle.

For ease of discussion, the absorbent article will be discussed with reference to the numerals referred to in these figures. The figures and detailed description should however not be considered limiting the scope of the claims, unless explicitly indicated otherwise, and the invention disclosed herein is also used in a wide variety of absorbent article forms.

BRIEF DESCRIPTION OF THE DRAWINGS

In the drawings, like numerals or other designations designate like features throughout the views.

Figures 1, 3:
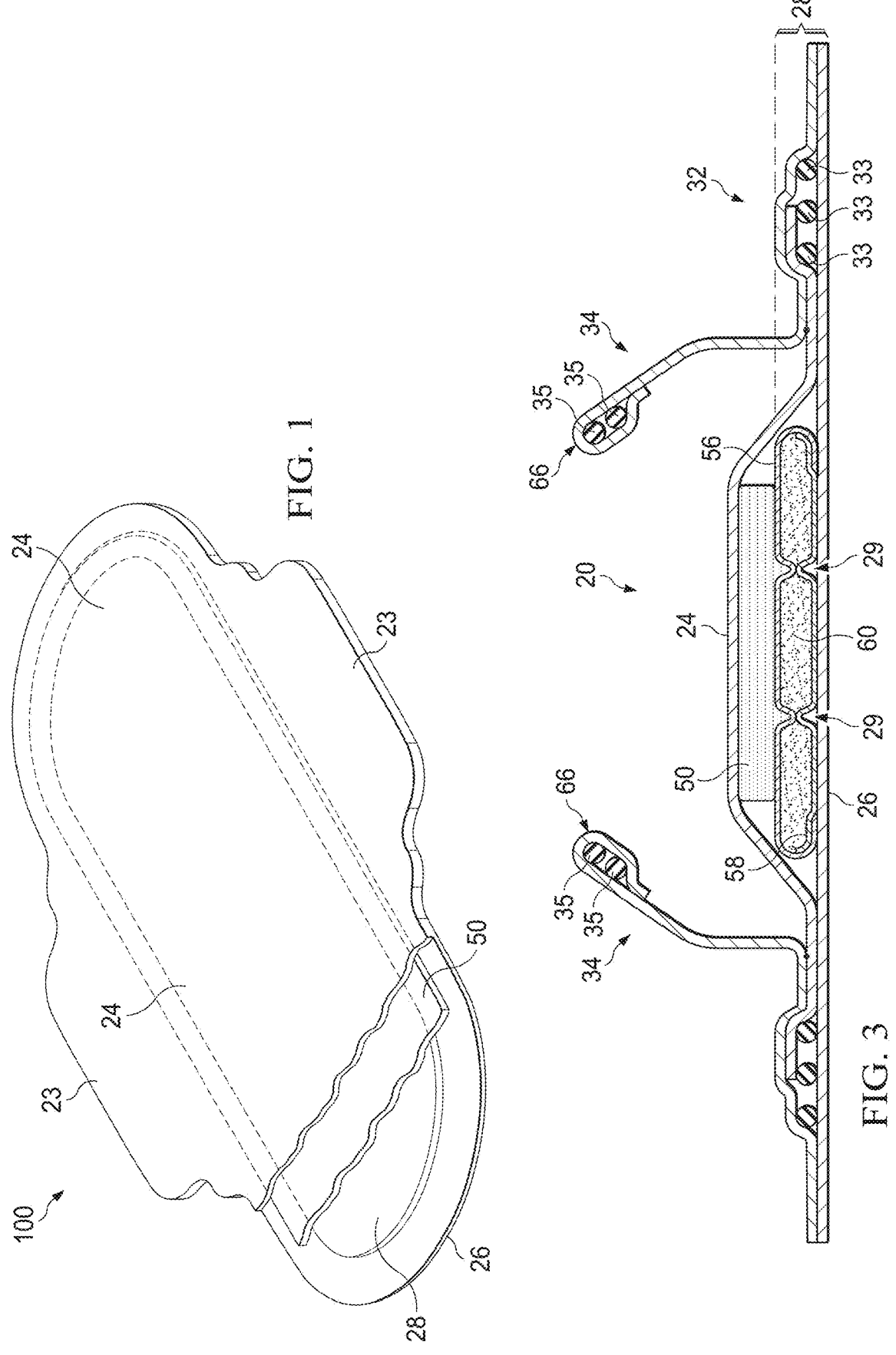
FIG. 1 is a perspective view of an exemplary absorbent article.
FIG. 3 is a lateral cross-section view along 3-3 of the absorbent article of FIG. 2.

DETAILED DESCRIPTION OF THE
INVENTION

Various non-limiting forms of the present disclosure will now be described to provide an overall understanding of the principles of the structure, function, manufacture, and use of an absorbent article comprising an apertured topsheet comprising cellulose-based fibers having mitigated rewet and improved stain masking. One or more examples of these non-limiting embodiments are illustrated in the accompanying drawings. Those ordinary skilled in the art will understand that the absorbent articles described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

"Absorbent article" refers to wearable devices, which absorb and/or contain liquid, and more specifically, refers to devices, which are placed against or in proximity to the body of the wearer to absorb and contain the various exudates discharged from the body. Absorbent articles can include diapers, training pants, adult incontinence undergarments, feminine hygiene products such as sanitary napkins, menstrual pants, and pantyliners, and wipes.

As used herein, the term "comprising" means that the various components, ingredients, or steps can be conjointly employed in practicing the present invention. Accordingly, the term "comprising" is open-ended and encompasses the more restrictive terms "consisting essentially of" and "consisting of".

As used herein, the term "cellulose-based fibers" intends to include both natural cellulose fibers such as pulp and cotton, and regenerated cellulose fibers such as rayon (including viscose, lyocell, MODAL (a product of Lenzing AG, Lenzing, Austria) and cuprammonium rayon) unless specified differently.

As used herein, the terms "hydrophilic" and "hydrophobic" have meanings that are well established in the art with respect to the contact angle of water on the surface of a material. Thus, a material having a water contact angle of greater than about 90° as measured by Contact Angle Test is considered hydrophobic, and a material having a water contact angle of less than about as measured by Contact Angle Test is considered hydrophilic.

As used herein, the term "natural fibers" refers to elongated substances produced by plants and animals and comprises animal-based fibers and plant-based fibers. Natural fibers may comprise fibers harvested without any post-harvest treatment step as well as those having a post-treatment step, such as, for example, washing, scouring, and bleaching.

As used herein, the term "plant-based fibers" comprises both harvested fibers and synthetic fibers that comprise bio-based content. Harvested plant-based fibers may comprise cellulosic matter, such as wood pulp; seed hairs, such as cotton; stem (or bast) fibers, such as flax and hemp; leaf fibers, such as sisal; and husk fibers, such as coconut.

Absorbent Article

Absorbent articles will now be generally discussed and further illustrated in the form of a sanitary napkin 100 as exemplarily represented in FIG. 1. FIG. 1 is a plan view of the exemplary sanitary napkin 100 in a flattened-out configuration and the garment facing side turned up. As shown in FIG. 1, an absorbent article according to the present invention, a sanitary napkin 100 for example, comprises a topsheet 24 having a wearer facing surface and a garment facing surface (not shown in FIG. 1) positioned opposite to the wearer facing surface. The absorbent article further comprises a backsheet 26 having a garment facing surface and a user facing surface positioned oppositely to the garment facing surface, the backsheet 26 being at least partially joined to the topsheet 24. The absorbent article also comprises an absorbent core 28 positioned between the topsheet 24 and the backsheet 26. The absorbent article may further comprise an optional acquisition and/or distribution layer (or system) or a secondary topsheet 50 is represented and/or a pair of flaps or wings 23. The topsheet 24, the backsheet 26, and the absorbent core 28 can be assembled in a variety of well-known configurations.

The backsheet 26 and the topsheet 24 can be secured together in a variety of ways. The topsheet 24 and the backsheet 26 can be joined to each other by using an adhesive, heat bonding, pressure bonding, ultrasonic bonding, dynamic mechanical bonding, or a crimp seal. A fluid impermeable crimp seal can resist lateral migration ("wicking") of fluid through the edges of the product, inhibiting side soiling of the user's undergarments.

When the absorbent article is a sanitary napkin as shown in FIG. 1, as is typical for sanitary napkins and the like, the sanitary napkin can have panty-fastening adhesive disposed on the garment facing side of backsheet 26. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the user's panties.

Figure 2:
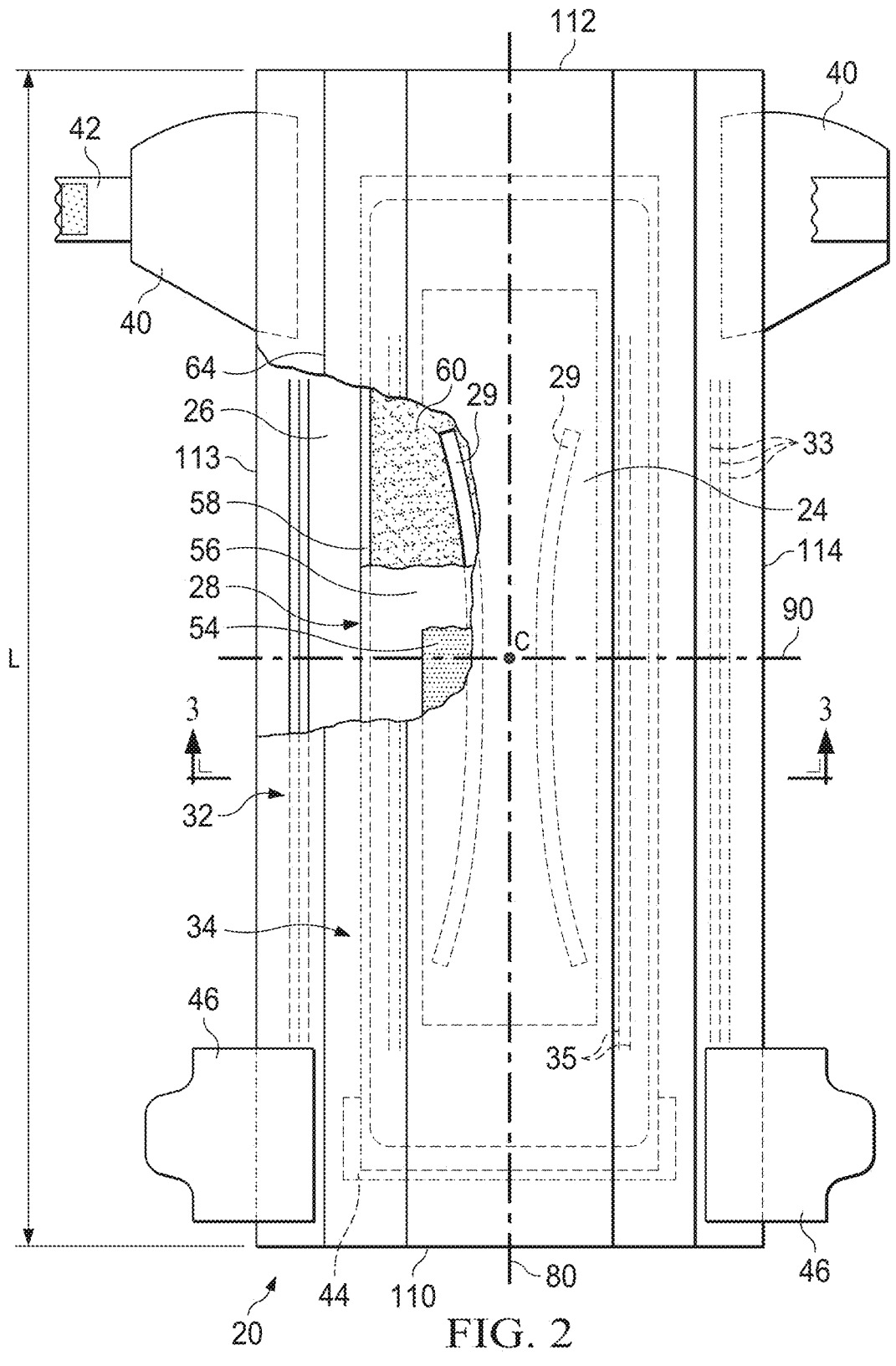
FIG. 2 is a schematic plan view of an exemplary absorbent article.

Absorbent articles will be generally further illustrated in the form of a baby diaper 20 as exemplarily represented in FIG. 2. FIG. 2 is a plan view of the exemplary diaper 20 in a flattened-out configuration with the taped ends opened and the garment-facing side turned up. An article that is presented to the user closed such as a training pant may also be represented flattened out by cutting it along its side waists. The absorbent article will typically have a front edge 110, a back edge 112 and the longitudinally-extending lateral side edges 113, 114. The front edge 110 forms the edge of the front waist and the back edge 112 of the back waist, which together when worn by the wearer form the opening for the waist of the wearer. The lateral edges 113, 114 can each form one of the leg openings. The absorbent article 20 notionally comprises a longitudinal centerline 80 dividing the article in a left side and a right side, and a perpendicular transversal centerline 90 disposed at half the length of the article as measured on the longitudinal centerline 80, with both centerlines crossing at the center point C. The taped back ends 42 attached on the front of the diaper to such as a landing zone 44.

Other layers of the absorbent article are better illustrated in FIG. 3, which shows in cross-section in addition to the liquid permeable topsheet 24 and the backsheet 26, an absorbent core 28 between the topsheet 24 and the backsheet 26.

An optional acquisition and/or distribution layer (or system) 50 is represented in FIG. 3 together with other typical diaper components. The acquisition and/or distribution layer may comprise one layer or more than one layer. Typical acquisition and/or distribution layers may not comprise SAP as this may slow the acquisition and distribution of the fluid, but an additional layer may also comprise SAP if some fluid retention properties are wished.

The absorbent article may typically comprise a pair of partially upstanding barrier leg cuffs 34 having elastic elements 35 and elasticized gasketing cuffs 32 having elastic elements 33 substantially planar with the chassis. Both types of cuffs are typically joined to the chassis of the absorbent article typically via bonding to the topsheet and/or backsheet.

The absorbent article may comprise elasticized back ears 40 having a tape end 42 which can be attached to a landing zone 44 at the front of the article, and front ears 46 typically present in such taped diapers.

Topsheet Comprising Cellulose-Based Fibers

The topsheet is generally liquid permeable and is configured to receive the fluids being excreted from the body and aid in directing the fluids toward an acquisition system/distribution layer (system), and/or the absorbent core. One of the important qualities of a topsheet is the ability to reduce ponding of the fluids on the topsheet before the fluids are able to be absorbed by the absorbent article. Another desirable quality of a topsheet is to reduce rewet of the topsheet. It is also desirable that the topsheet is to present a clean user contacting surface with less stain.

The topsheet in the present the invention is the part of the absorbent article that is in contact with the wearer's skin during use of the article. The topsheet may be joined to portions of the backsheet, the absorbent core, and/or any other layers as is known to those of ordinary skill in the art.

Further, at least a portion of, or all of, the topsheet may be liquid permeable, permitting liquid bodily exudates to readily penetrate through its thickness.

The topsheet of the present invention comprises cellulose-based fibers and may further comprise synthetic fibers such as thermoplastic fibers.

The topsheet in the present the invention comprises a first layer comprising cellulose-based fibers. The topsheet may be formed of a single layer, of two layers, or, of more than two layers.

Synthetic fibers may be selected from the group consisting of polyesters, polypropylenes, polyethylenes, polyethers, polyamides, polyhydroxyalkanoates, polysaccharides, and combinations thereof. Additionally, other synthetic fibers such as rayon, polyethylene, and polypropylene fibers can be used within the scope of the present disclosure.

Thermoplastic fibers may be single component fibers (i.e., single synthetic material or a mixture to make up the entire fiber), multicomponent fibers, such as bicomponent fibers (i.e., the fiber is divided into regions, the regions including two or more different synthetic materials or mixtures thereof), and combinations thereof.

The topsheet may also comprise semi-synthetic fibers made from polymers, specifically hydroxyl polymers. Non-limiting examples of suitable hydroxyl polymers include polyvinyl alcohol, starch, starch derivatives, chitosan, chitosan derivatives, cellulose derivatives such as viscose, gums, arabinans, galactans, Lyocell (Tencel®) and combinations thereof.

Cellulose-based fibers may be selected from the group consisting of wheat straw fibers, rice straw fibers, flax fibers, bamboo fibers, cotton fibers, jute fibers, hemp fibers, sisal fibers, bagasse fibers, hesperaloe fibers, and combinations thereof.

The topsheet in the present invention may comprise a woven or nonwoven web.

Several examples of nonwoven materials suitable for use as a topsheet may include, but are not limited to: spunbonded nonwovens; carded nonwovens; carded air through nonwovens; spunlace nonwovens, needle punched nonwovens and nonwovens with relatively specific properties to be able to be readily deformed.

The nonwoven web can be formed from many processes, such as, for example, air laying processes, wetlaid processes, meltblowing processes, spunbonding processes, needle punching processes and carding processes. The fibers in the nonwoven web can then be bonded via spunlacing processes, hydroentangling, calendar bonding, through-air bonding and resin bonding.

The topsheet may comprise a spunlace nonwoven.

The topsheet may have a basis weight from about 10 to about 200 g/m$^2$, or from about 20 to about 100 g/m$^2$, or about 25 to about 60 g/m$^2$, or about 30 to about 50 g/m$^2$.

First Layer

The first layer comprises cellulose-based fibers and may be a woven or nonwoven web. The first layer may further comprise thermoplastic fibers.

The list of thermoplastic fibers and of cellulose-based fibers, and the nonwoven web manufacturing process correspond to the list and process disclosed above for the topsheet.

Cotton fibers are natural cellulosic fibers that have good liquid acquisition, good breathability and good softness. Therefore, having a topsheet comprising a first layer of cotton fibers improves the softness of the topsheet while improving the fluid handling properties of the topsheet.

The first layer comprises at least 15% by weight, or at least 30% by weight, or at least 50% by weight, or at least 60% by weight, or at least 75% by weight, or at least 95% by weight of cellulose-based fibers, such as cotton fibers and rayon fibers, by total weight of the first layer. The first layer may be made of 99% to 100% by weight cellulose-based fibers, such as cotton fibers and rayon fibers, by total weight of the first layer.

As the first layer of the topsheet faces the skin of the wearer of the absorbent article during use of the article, having a high content of cellulose-based fibers, in the first layer of the topsheet enables to have a soft feel for the wearer's skin as well as to increase the amount of biodegradable material in contact with the wearer's skin and to decrease the risk of allergies, irritations or rashes on the skin of the wearer.

The first layer comprises a first surface, an opposite second surface and a plurality of apertures. The first surface of the first layer comprises at least one non-aperture area which has no aperture.

The non-aperture area may fully surround the apertures. The non-aperture area may together form a generally continuous grid throughout the first surface of the first layer, while the apertures may be discrete elements dispersed in and surrounded by the continuous grid.

The non-aperture area may be a plurality of discrete areas defined by apertures. Each of the plurality of discrete non-aperture areas has a periphery formed by a continuous line of apertures, with adjacent apertures being spaced apart by an edge-to-edge distance of no more than 3 mm. Further, each of the plurality of discrete non-aperture areas is substantially free of apertures within the periphery. At least some of said plurality of discrete non-aperture areas may be sufficiently large, i.e., having an area of about 50 $mm^2$ or more, or about 60 $mm^2$ or more, as measured according to Non-Aperture Area Size Measurement.

The non-aperture area may be a land area or a protrusion.

The non-aperture area is hydrophilic and has a first non-aperture area contact angle. The first non-aperture area contact angle may be no greater than about 15°, or no greater than about or no greater than about 5°, as measured by Contact Angle Test. The non-aperture area may comprise hydrophilic fibers, or fibers treated with a hydrophilic treatment.

Hydrophobic fibers may be rendered hydrophilic by treatment with a hydrophilic treatment such as a hydrophilic surfactant, e.g., by spraying hydrophobic fibers with a hydrophilic treatment, by dipping the fiber into a treatment or by including a hydrophilic treatment as part of the polymer melt in producing thermoplastic fibers. Upon melting and resolidification, the treatment will tend to remain at the surfaces of the fiber.

The non-aperture area of the first surface may be free of a treatment. The non-aperture area of the first surface may comprise a hydrophilic treatment.

The first layer comprises a plurality of apertures. Each of majority of the plurality of apertures comprises a side wall having an aperture contact angle as measured by Contact Angle Test, the aperture contact angle being higher than the first non-aperture area contact angle. The aperture contact angel may be equal to or higher than about 40°, or equal to or higher than about or equal to or higher than about 50°, as measured by Contact Angle Test. The aperture contact angle may be higher than the first non-aperture area contact angle by at least 20°, or by at least 30°, or by at least 40°.

The side wall of each aperture may be treated with a treatment such as a treatment with a HLB value not higher than about 13.

The HLB values for commonly-used treatments are readily available in the literature (e.g., HLB Index in *McCutcheon's Emulsifiers and Detergents*, MC Publishing Co., 2004). Another way of obtaining HLB values is to estimate by calculations. The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20. Other examples of how to calculate HLB values are described by Davies in *Interfacial Phenomena,* 2nd Edition, Academic Press, London, 1963 and by Lin in *J. Phys. Chem.* 76, 2019-2013, 1972.

The first layer may comprise a mixture of hydrophobic fibers and hydrophilic fibers. The amount of hydrophilic fibers may be higher than the amount of hydrophobic fibers. For example, the first layer may comprise a mixture of from 5% to 40% by weight of hydrophobic fibers and from 60% to 95% by weight of hydrophilic fibers by total weight of the first layer. For example, the first layer may comprise a mixture of from 5% to 40% by weight of hydrophobic synthetic fibers and from 60% to 95% by weight of hydrophilic cellulose-based fibers by total weight of the first layer.

The first layer may be a spunlace nonwoven layer. The spunlace layer may be composed of a carrier web and of a web comprising cellulose-based fibers with part of the web comprising cellulose-based fibers entering the carrier web. The carrier web may be a nonwoven web.

The web comprising cellulose-based fibers may be formed on one side of the carrier web. Cellulose-based fibers of the natural fiber web may enter the fiber network of the carrier web and interlace with the fiber network. Understandably, the cellulose-based fibers may interlace with each other. The carrier web may also interlace with the web comprising cellulose-based fibers.

The carrier web may be made of different types of synthetic fibers. The carrier web may be made also of cellulosic fibers.

The first layer may have various structures.

Figure 4A:
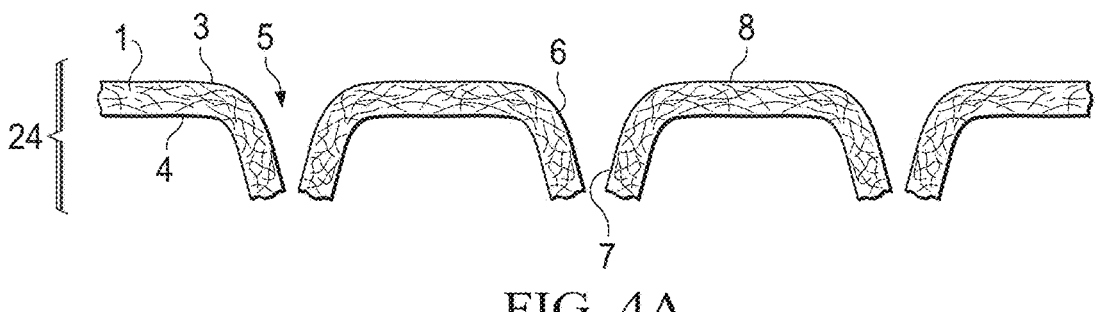
FIG. 4A is a schematic view of a topsheet having a flat first layer in accordance with the present invention.

Referring to FIG. 4A, the topsheet 24 comprises at least a first layer 1. The first layer 1 comprises a first surface 3 and a second surface 4.

The first layer 1 comprises a plurality of apertures 5. To ensure material stability, the smallest edge-to-edge distance between the majority of the apertures regardless of their particular shape and width is at least 0.5 mm, or at least 1.5 mm or 2.0 mm. This distance is measured on the first surface 3 of the first layer 1 of the topsheet.

The apertures may vary in shape. For example, the shape of the apertures as seen from the first surface of the first layer may be circular, elliptic, rectangular or polygonal. In one embodiment, the apertures have a circular shape, an elliptic shape or a polygonal shape.

The tridimensional shape of the apertures may be cylindrical (e.g. with a circular or elliptic base), prismatic (e.g. with a polygonal base) or truncated cone or pyramidal.

Each of the apertures 5 has a side wall 6. The side wall 6 may extend outwardly, away from land area 8 of the second surface of the first layer, as shown in FIG. 4A. When the topsheet described herein is incorporated into an absorbent article, the direction of the side walls of the apertures, when extending outwardly, may be towards the absorbent core of the absorbent article.

The amount of extension of the side walls of the apertures may be at least 0.1 mm beyond the second surface of the first layer, or at least 0.2 mm beyond the second surface of the first layer. The side walls of the apertures may form funnels or channels.

Figure 4B:
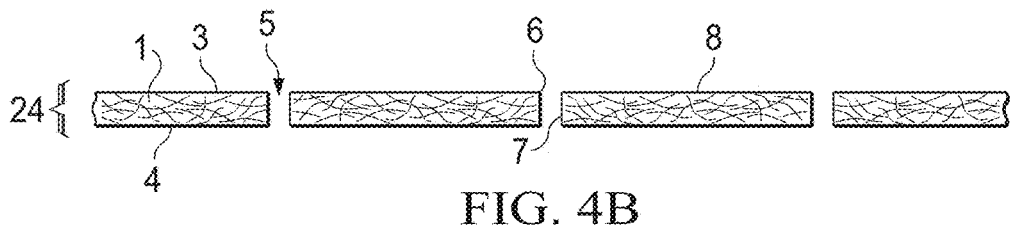
FIG. 4B is a schematic view of a topsheet having a flat first layer in accordance with the present invention.

The side wall 6 may not extend outwardly as shown in FIG. 4B.

The apertures may be tapered and take a conical shape such that the diameter of the aperture is larger at a part of the aperture proximate to the first surface of the first layer than the diameter of the aperture at the bottom edge of the aperture.

Such tapered configuration helps to reduce the risk of rewet, i.e. of body liquids passing back from components underneath the topsheet (such as the absorbent core) into and through the topsheet. With apertured hydrophobic topsheets, rewet occurs predominantly through the apertures. The tapered shape of the apertures can help to reduce rewet, as the diameter of the aperture towards the absorbent core is smaller than the diameter of the aperture in the first layer.

The plurality of apertures may also vary in width.

The majority of the apertures may comprise a treatment.

The treatment may be applied via pin coating described in detail later or other application processes known in the art. The treatment can be applied to the majority of the apertures via aperturing forming process such as the pin aperturing processes, or via printing processes.

The apertures of the first layer of the topsheet may have at least 2.5% of open area, or at least 3% of open area, or at least 3% of open area. The apertures of the first layer of the topsheet may have an open area no greater than about 10%, or no greater than 8%.

Each of majority of the apertures, or at least 70% of the apertures, or at least 80% of the apertures, or at least 90% of the apertures has a side wall having an aperture contact angle as measured by Contact Angle Test, the aperture contact angle being higher than the first non-aperture area contact angle.

The size of apertures may be determined to achieve the desired fluid and/or air penetration performance and other performances expected by wearers. If the apertures are too small, the fluids may not pass through the apertures, either due to poor alignment of the fluid source and the aperture location or due to runny fecal masses, for example, having a diameter greater than the apertures. If the apertures are too large, the area of skin that may be contaminated by "rewet" from the article is increased.

When the majority of the apertures have side walls having an aperture contact angles higher than the first non-aperture area contact angle, each of the plurality of apertures may have a size ranging from 0.2 mm$^2$ to 1.5 mm$^2$, from 0.2 mm$^2$ to 1.0 mm$^2$, or from 0.25 mm$^2$ to 0.5 mm$^2$, and/or a diameter ranging from 0.3 mm to 1.5 mm, or from 0.3 mm to 1 mm, or from 0.4 mm to 0.8 mm. The plurality of apertures may have regular shapes selected from the group consisting of circle, oval, triangle, square, rectangle, parallelogram, trapezoid, polygon, hourglass, star, and any combinations thereof.

Apertures in the topsheet in the present invention are less likely to trap or retain fluid by fibers or in between fibers thanks to sidewalls having an aperture contact angle higher than the first non-aperture area contact angle, preferably higher than about 40° as measured by Contact Angle Test. Therefore, the topsheet disclosed herein provides improved fluid handling properties such as a reduced rewet onto the wearer-facing surface of the absorbent article and a good stain masking without compromising fluid acquisition speed.

Figure 5:
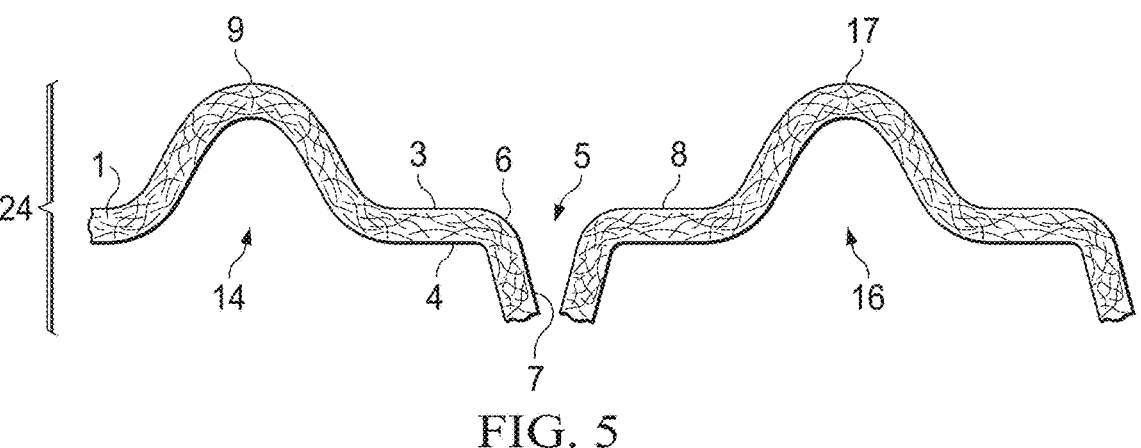
FIG. 5 is a schematic view of a topsheet having a three-dimensional first layer in accordance with the present invention.

According to FIG. 5, the first layer 1 may comprise a plurality of protrusions 9. The first layer 1 comprises a plurality of apertures 5. The first layer 1 comprises land area 8 between the majority of the apertures 5. The land area may be substantially flat.

The majority of the protrusions 9 may protrude outwardly from the land area 8 of the first layer 1 of the topsheet 24.

The first layer 1 has a first surface 3 and a second surface 4. The majority of the protrusions 9 may be located on the first surface 3 of the first layer 1. The majority of the protrusions 9 may extend outward from the first surface 3 of the first layer 1.

The plurality of the protrusions 9 may be uniformly distributed on the first surface 3 of the first layer 1. The plurality of the protrusions 9 may be unevenly distributed and form a shape or a pattern on the first surface 3 of the first layer 1. The majority of the protrusions 9 may be provided throughout the complete surface of the first layer 1 or may only be provided in a portion of the first layer 1.

The majority of the protrusions 9 may be surrounded by a plurality of land area 8 and/or a plurality of apertures 5.

The plurality of land area 8, the plurality of apertures 5 and the plurality of protrusions 9 may form a three-dimensional surface on the first surface 3 of the first layer 1 of the topsheet 24.

Alternatively, the protrusions 9 may extend outward from the second surface 4 of the first layer 1. In this case, the protrusions 9 may be named "recesses". The term "recesses" corresponds to protrusions of a topsheet that protrude away from the skin of the wearer when the topsheet is incorporated into an absorbent article. The plurality of land area 8, the plurality of apertures 5 and the plurality of protrusions 9 may form a three-dimensional surface on the second surface 4 of the first layer 1 of the topsheet 24.

The majority of the protrusions 9 may be hollow.

When viewing from the first surface 3 of the first layer 1, the majority of the protrusions 9 may protrude from the land area 8 of the first layer 1 in the same direction.

When the topsheet described herein is incorporated into an absorbent article, the plurality of protrusions may protrude toward the skin of the wearer when the article is in use and away from the absorbent core of the absorbent article.

Alternatively, when the topsheet described herein is incorporated into an absorbent article, the plurality of protrusions may protrude towards the absorbent core of the absorbent article.

Viewed from a cross-sectional view, i.e. in a Z-direction, the majority of the protrusions 9 may have any suitable shapes which include, but are not limited to: cylindrical, bulbous-shaped, conical-shaped and mushroom shaped.

Viewed from above, the majority of the protrusions 9 may have any suitable shapes which include, but are not limited to: circular, dome-shaped, diamond-shaped, round diamond-shaped, oval-shaped, clover-shaped, triangular-shaped, teardrop shaped and elliptical-shaped protrusions.

The majority of the protrusions 9 may comprise an inside void volume 14 which is the portion of the protrusion which does not comprise any fibers or very little fibers. The void volume 14 can improve the breathability of the topsheet. The majority of the protrusions 9 may provide void volume to receive the body fluids.

This three-dimensional first layer of the topsheet provides better softness to the topsheet. It also helps maintain the skin of the wearer away from body fluids in the land area as the protrusions essentially create a space between the skin of the wearer and the body fluids.

Second Layer:

The topsheet may further comprise a second layer which comprises a first surface, an opposing second surface in such a way that the first surface of the second layer is in a face to face relationship with the second surface of the first layer.

All aspects described above for the first layer are equally applicable to the second layer in a topsheet which comprising a first and a second layers.

The second layer may be a woven or nonwoven web of natural fibers, synthetic fibers or a combination of natural and synthetic fibers. In one embodiment, the second layer comprises thermoplastic fibers.

Natural fibers may be selected from the group consisting of wheat straw fibers, rice straw fibers, flax fibers, bamboo fibers, cotton fibers, jute fibers, hemp fibers, sisal fibers, bagasse fibers, hesperaloe fibers, miscanthus, marine or fresh water algae/seaweeds and combinations thereof.

The list of synthetic fibers corresponds to the list disclosed above for the topsheet and the first layer.

The second layer may have a plurality of apertures at least partially aligned with the apertures of the first layer. All apertures of the second layer may be aligned with the apertures of the first layer. This may be achieved by forming the apertures of the first layer and of the second layer simultaneously after the first and second layer have been placed in a face to face relationship.

Figure 6:
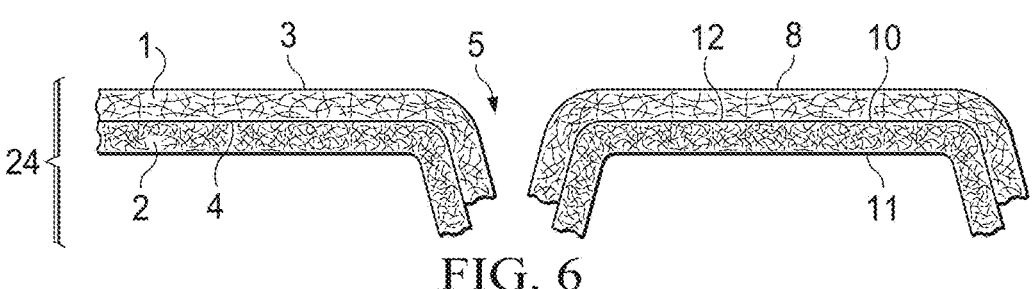
FIG. 6 is a schematic view of a topsheet having a first layer and a second layer in accordance with the present invention.
Figure 7A:
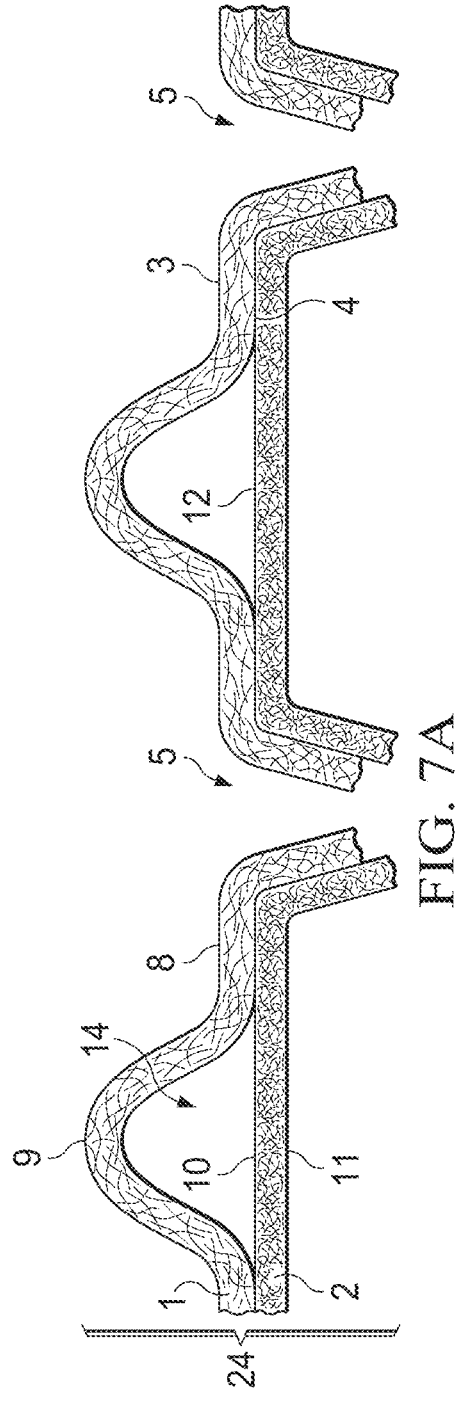
FIG. 7A is a schematic view of a topsheet having a three-dimensional first layer and a flat second layer in accordance with the present invention.
Figure 7B:
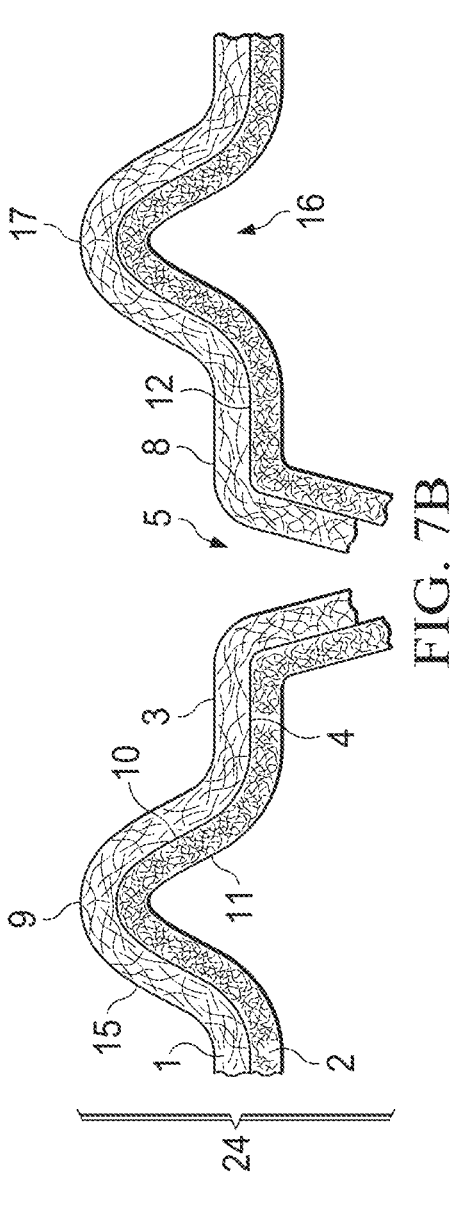
FIG. 7B is a schematic view of a three-dimensional topsheet having a first layer and a flat second layer in accordance with the present invention.

Referring to FIGS. 6-7B, the first layer 1 may at least partially penetrate the second layer 2 of the topsheet 24 at the apertures 5. This characteristic may be facilitated according to the process described below.

Alternatively, the first layer may not penetrate the second layer of the topsheet at the apertures. This characteristic may be formed by using an alternative process such as the process described in U.S. Pat. No. 5,628,097, or with a hole puncher.

Each of the apertures 5 in the second layer has a side wall 6. The side wall 6 may extend outwardly, away from land area 12 of the second surface of the second layer, as shown in FIGS. 6-7B. When the topsheet described herein is incorporated into an absorbent article, the direction of the side walls of the apertures, when extending outwardly, may be towards the absorbent core of the absorbent article. The amount of extension of the side walls of the apertures may be at least 0.1 mm beyond the second surface of the second layer, or at least 0.2 mm beyond the second surface of the second layer. The side walls of the apertures may form funnels or channels.

When the topsheet described herein is incorporated into an absorbent article, the direction of these side walls may be towards the absorbent core of the absorbent article, or may be towards the skin of the wearer when the article is in use.

Descriptions relating to apertures correspond to the descriptions relating to apertures disclosed above for the first layer.

Referring to FIG. 6, the topsheet 24 may comprise a first layer 1 and a second layer 2. The first layer may comprise a first surface 3 and a second surface 4. The second layer may comprise a first surface 10 and a second surface 11.

The first surface 10 of the second layer 2 may be in contact with the second surface 4 of the first layer 1.

The second layer 2 may have a plurality of apertures 5. The first layer 1 has a plurality of apertures 5. The second layer 2 may have a plurality of apertures 5 at least partially aligned, or fully aligned with the apertures 5 of the first layer 1. The apertures 5 of the first layer 1 and of the second layer 2 may be the same. The plurality of apertures 5 of the second layer 2 may have the same width and/or length as the apertures 5 of the first layer 1.

The second layer 2 may comprise land areas 12 between the majority of the apertures 5. The land area 8 of the first layer 1 may be aligned with the land area 12 of the second layer 2.

The land area 12 of the second layer 2 may fully surround the apertures 5 of the first layer 1 and of the second layer 2.

The land area 12 of the second layer 2 may be substantially flat areas.

The land area 8, 12 in the first layer 1 and the second layer 2 may together form a generally continuous grid through the first layer 1 and the second layer 2, while the apertures 5 may be discrete elements dispersed throughout the first layer 1 and the second layer 2.

In one embodiment, the second surface of the second layer has at least one non-aperture area which has no aperture and a second non-aperture area contact angle, and the second non-aperture area contact angle is not greater than the first non-aperture area contact angle.

The first layer and the second layer may be in contact with each other and may be joined with each other at the non-aperture area and/or at the apertures 5.

The first layer and the second layer may be joined together or attached to each other through mechanical bonding, adhesive bonding, pressure bonding, heat bonding, passing heated air through both layers, or by other methods of joining to form the topsheet known in the art.

In one embodiment, the first layer is attached to the second layer in bonding areas by hot melt adhesive. Having a hydrophilic hot melt adhesive attaching the first layer and the second layer can help to have a low run-off of liquid.

In one embodiment, the first layer that first layer is partially interpenetrated to second layer in apertures where the first layer penetrates into apertures is phobic treated. With this feature, the first layer having a higher contact angle may act like a barrier against fluid-back from the second layer and the absorbent core, so that rewet cause by fluid-back from the second layer and the absorbent core may be mitigated or prevented. Referring to FIG. 6, in addition, the second layer is not completely covered by the first layer in the apertures, and the second layer is exposed in an area of the apertures proximate to the bottom edge of the aperture. Having such a feature, even though the first layer in the apertures has a higher contact angle, the second layer in the apertures having a lower contact angle and hydrophilic still helps liquid to pass through the apertures.

Referring to FIG. 7A, the topsheet may comprise a three-dimensional first layer 1 and a flat second layer 2. The first layer may comprise a first surface 3 and a second surface 4. The second layer may comprise a first surface 10 and a second surface 11.

The first surface 10 of the second layer 2 may be in contact with and joined to the second surface 4 of the first layer 1.

The first layer 1 may have a plurality of protrusions 9 protruding from the land area 8 of the first layer 1 of the topsheet 24. The majority of the protrusions 9 may comprise an inside void volume 14 which is the portion of the protrusion which does not comprise any fibers or very little fibers. The void volume 14 can improve the breathability of the topsheet.

Referring to FIG. 7B, the topsheet 24 may be a laminate comprising the first layer 1 as previously described and a second layer 2 as previously described in a face to face relationship. In other words, the first layer 1 and the second layer 2 are joined to form a laminate.

The first layer 1 and the second layer 2 may be aligned in a face to face relationship such that the second surface 4 of the first layer 1 is in contact with the first surface 10 of the second layer 2. The first layer 1 and the second layer can be simultaneously mechanically deformed and combined to provide the topsheet having apertures and optional protrusions. This means that both the first layer 1 and the second layer 2 can be mechanically deformed and combined at the same time.

When the first layer and the second layer comprise a plurality of protrusions 9, the plurality of protrusions 9 of the first layer may be at least partially aligned, or fully aligned with the plurality of protrusions 9 of the second layer 2. The protrusions 9 of the first layer 1 and of the second layer 2 may be the same.

The first layer 1 and the second layer 2 may comprise a plurality of recesses. The apertures 5 may be located between the majority of the recesses and/or within the majority of recesses. Some recesses may not have apertures 5 therein.

The plurality of recesses of the first layer may be aligned with the plurality of recesses of the second layer. The plurality of recesses of the first layer and of the second layer may be the same. The first layer and the second layer may be in contact with each other at the recesses.

When the topsheet described herein is incorporated into an absorbent article, the first surface 3 of the first layer 1 is facing towards the body of the wearer during use of the article and the second surface 4 of the first layer 1 is facing towards the backsheet. When the topsheet comprises a first layer 1 and a second layer 2, the first layer 1 is facing towards the body of the wearer and the second layer 2 is facing towards the backsheet.

Absorbent Core

As used herein, the term "absorbent core" refers to a component used or intended to be used in an absorbent article and which comprises an absorbent material and optionally a core wrap. As used herein, the term "absorbent core" does not include the topsheet, the backsheet and any acquisition-distribution layer or multilayer system, which is not integral part of the absorbent core. The absorbent core is typically the component of an absorbent article that has the most absorbent capacity of all the components of the absorbent article. The terms "absorbent core" and "core" are herein used interchangeably. The absorbent core can be manufactured in a wide variety of sizes and shapes, and may be profiled to have different caliper, hydrophilic gradients, superabsorbent gradients, densities, or average basis weights at different positions across the face of the product.

Referring to FIGS. 1-3, the absorbent core 28 can absorb and contain liquid received by the absorbent article and comprise an absorbent material 60 (not indicated in FIG. 1). Referring to FIGS. 2 and 3, The absorbent core 28 may comprise absorbent material free channels 29, through which the top side 56 of the core wrap may be bonded to the bottom side 58 of the core wrap. Of course, this is entirely optional, the absorbent core may also not have bonded channels, or even unbonded channels. The absorbent core may be rectangular, but it is also common to have a shaped area which is tapered in the area around the transversal centerline 90.

The absorbent material comprises a liquid-absorbent material commonly used in disposable absorbent articles such as comminuted wood pulp, which is generally referred to as airfelt or fluff. Examples of other suitable liquid-absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers, absorbent gelling materials, or any other known absorbent material or combinations of materials.

The absorbent material in the absorbent core can be any type. It can be an airfelt core comprising wood cellulose fibers such as pulp fibers mixed with SAP, or an airfelt-free core free from such cellulose fibers. Airfelt cores typically comprises from 40% to 80% of SAP. For absorbent cores comprising a relatively high proportion of SAP at least partially enclosed within the core wrap, the SAP content may represent in particular at least 80%, 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent core may comprise an absorbent material comprising at least 80%, at least 90%, at least 95%, or at least 99% by weight of the absorbent core. The term "superabsorbent polymer" (herein abbreviated as "SAP") refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example.

Backsheet

The backsheet that covers the lower side of the absorbent core prevents the fluids in the absorbent core from wetting articles that contact the sanitary napkin, such as undergarments. Accordingly, the backsheet can be made from a liquid impervious thin film or a liquid impervious but vapor pervious film/nonwoven laminate, a microporous film, an apertured formed film, or other polymer film that is vapor permeable, or rendered to be vapor permeable, but substantially impervious to fluid.

Method for Nonwoven Treatment with a Treatment Composition

When apertures in nonwoven comprise a treatment, the treatment may be applied to the nonwoven using a well known method such as pin aperturing processes and via printing processes. The treatment may be applied to the nonwoven simultaneously with aperture formation on the nonwoven using, for example, pin aperturing process comprising steps of: a) providing a first layer comprising cellulose-based fibers, a first surface and an opposite second surface, b) providing an aperturing apparatus comprising a first forming member and a second forming member which engages the first forming member, wherein the first forming member comprises a plurality of pins on its surface and the second forming member comprises a plurality of recesses on its surface, c) wetting the pins on the first forming member with a treatment, and d) moving the first layer between the first and second forming members so that apertures are formed in the first layer as the pins on the first forming member and the recesses on the second forming member are engaged and the apertures are treated with the treatment. When a nonwoven comprises a first layer and a second layer, a first layer comprising cellulose-based fibers, a first surface and an opposite second surface, and a second layer comprising a first surface and an opposite second surface are provided in such a way that the first surface of the second layer is in a face to face relationship with the second surface of the first layer to step d) so that apertures are formed on both the first layer and the second layer in step d).

Figure 8:
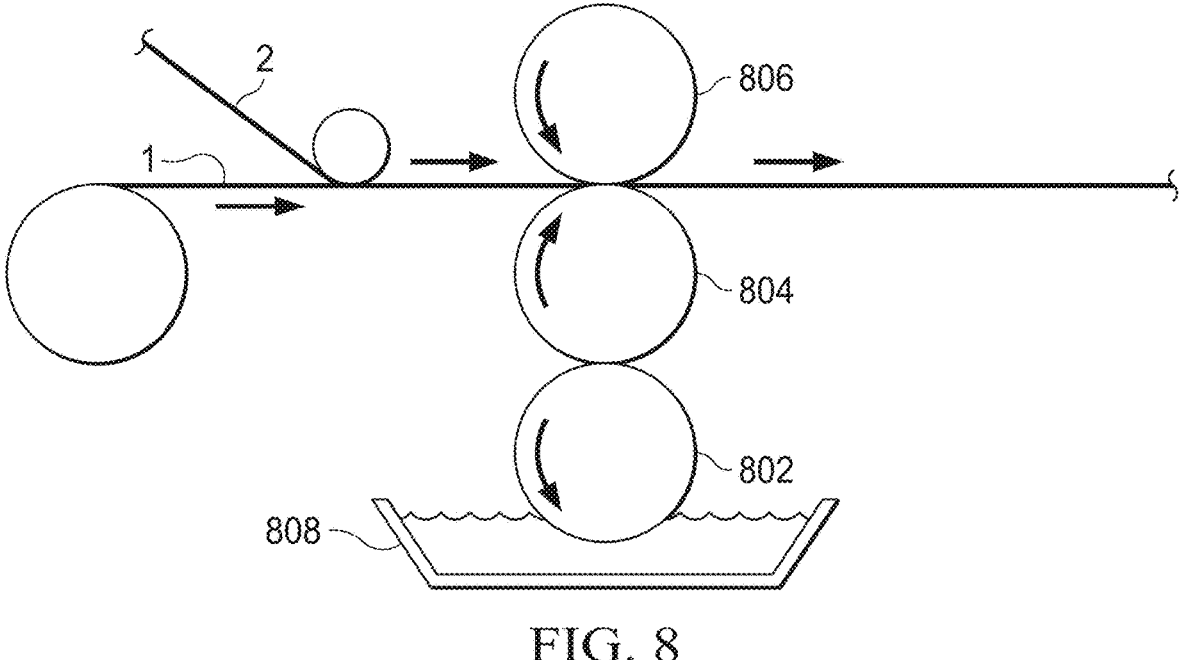
FIG. 8 is a schematic illustration of an apparatus for applying a treatment composition to a nonwoven substrate.
Figure 9A:
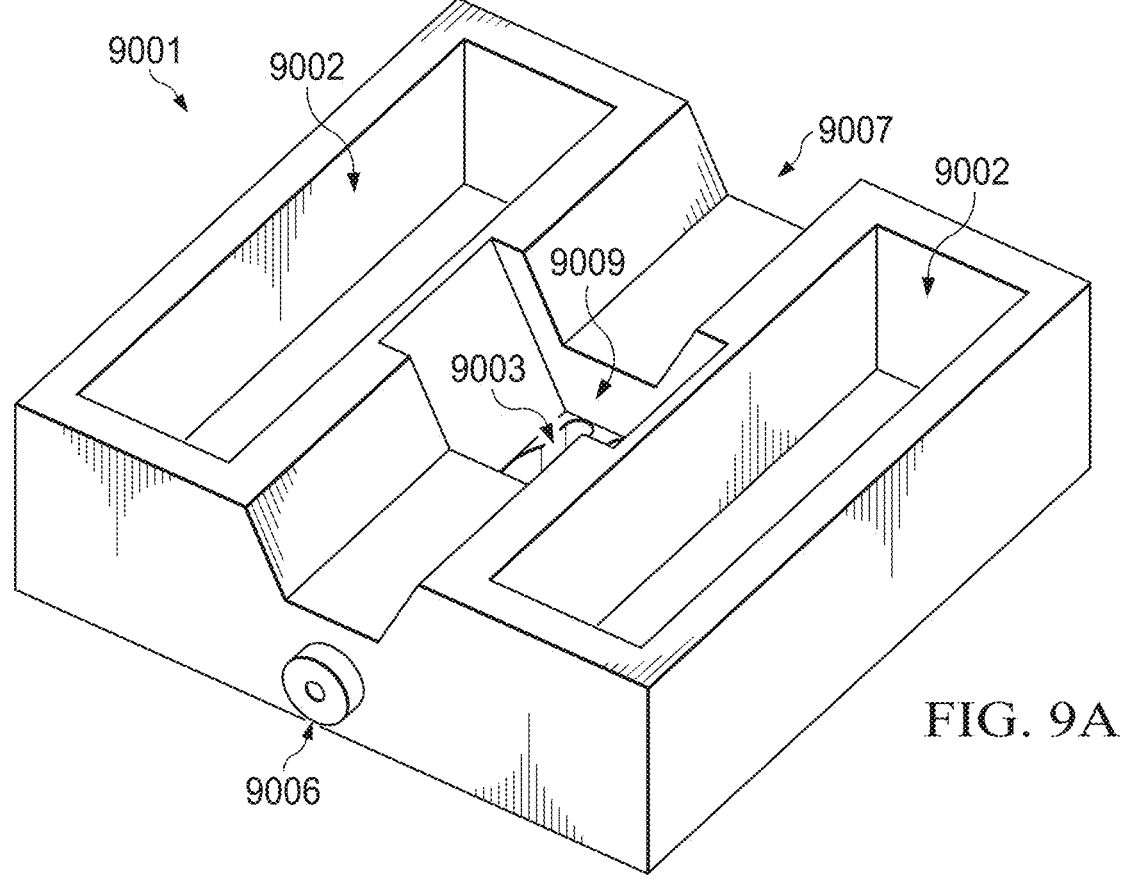
FIG. 9A is a perspective view of a strikethrough plate for acquisition time measurement.
Figure 9B:
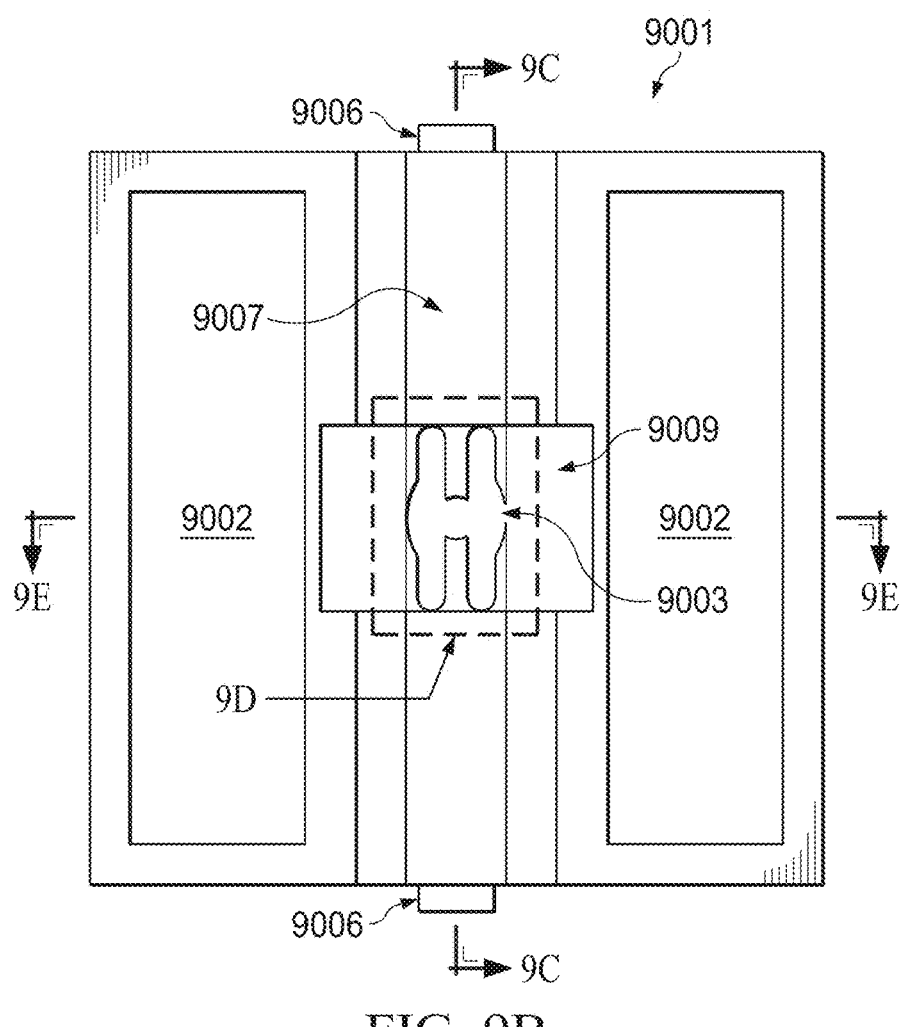
FIG. 9B is a plan view of the strikethrough plate of FIG. 9A.
Figure 9C:
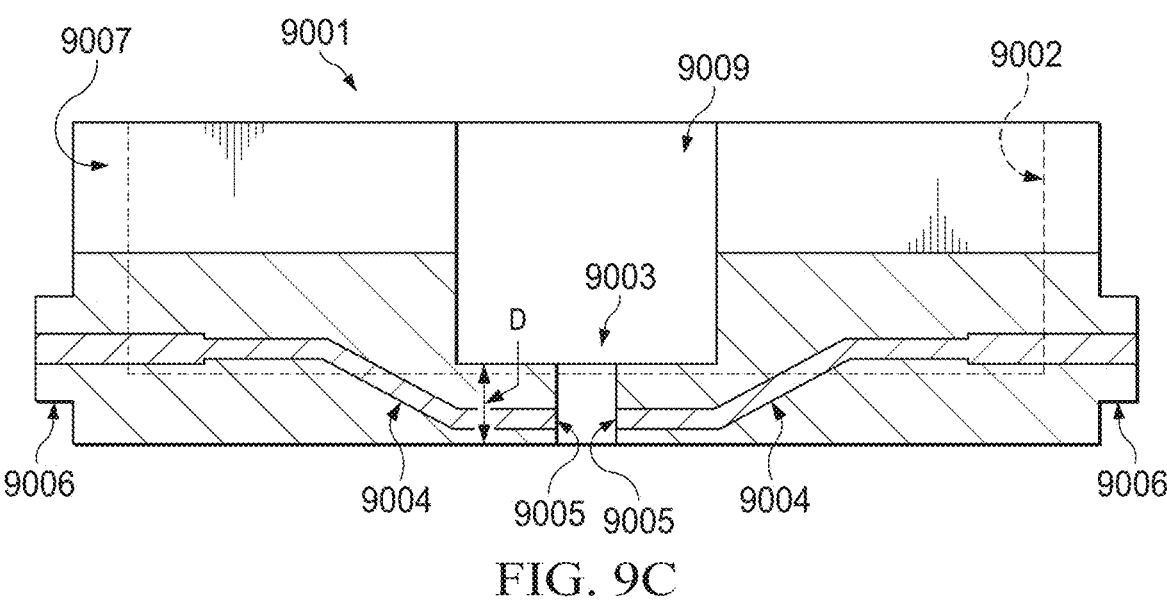
FIG. 9C is a plan view of a 9C-9C direction cross section of the strikethrough plate of FIG. 9B.
Figures 9D, 9E:
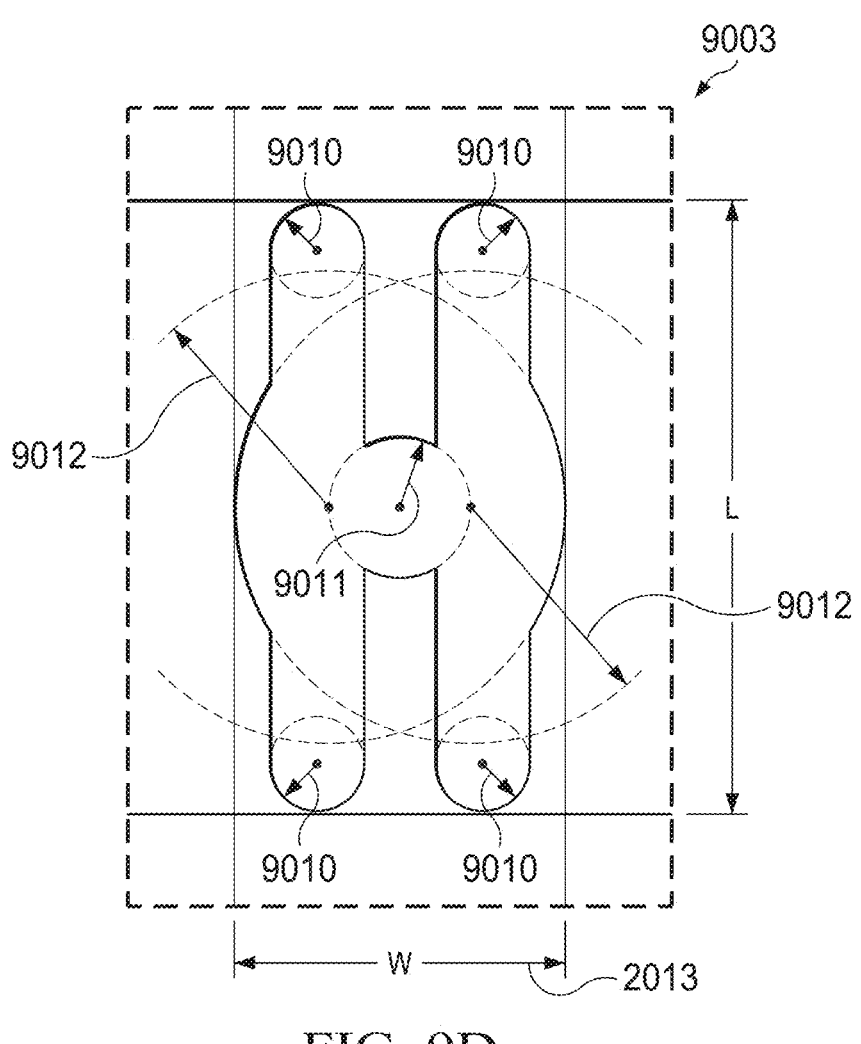
FIG. 9D is a plan view of part pf the strikethrough plate of FIG. 9B.
FIG. 9E is a plan view of a 9E-9E direction cross section of the strikethrough plate of FIG. 9B.

For example, aperturing pins process forming apertures and treating the apertures with a treatment may correspond to a process having three rolls wherein a first roll picks up the treatment from a container containing the treatment and transfers it to an intermediate roll comprising aperture forming elements. The intermediate roll intermeshes with a third roll to form apertures on a nonwoven and while wetting side walls of the apertures. The excess of hydrophobic surfactant may be removed with a vacuum roller. Referring to FIG. 8, a treatment composition is prepared and stored in a soaking tank 808. A first roll 802 is disposed in the soaking tank 808 so as to be at least partially submerged in the treatment in the soaking tank 808, so that, as the first roller 802 passes through the treatment, an amount of the treatment may be picked up and carried in in the surface of the first roller 802. The first roller 802 may comprise resilient or compressible surface such as rubber to effectively hold a certain amount of the treatment. A first forming member, a second roll 804 in this case, comprises a plurality of aperture-forming elements such as pins. A second forming member, a third roll 806 in this case, comprises a plurality of recesses. The aperture-forming elements in the first forming member 804 intermesh with the recesses in second forming member 806. A first layer 1 from a spool or otherwise is fed between a first forming member 804 and second forming member 806. As the first nonwoven layer is fed between the first forming member 804 and second forming member 806, the first forming member 804 may bring the first nonwoven layer 1 into contact with the aperture-forming elements of the first forming member 804 and the treatment thereon. Upon contact of the first nonwoven layer 1 with the aperture-forming elements of the first forming member 804, the first forming member 804 together with second forming member 806 create apertures in the first nonwoven layer 1 while wetting the side walls of the apertures with the treatment. Optionally a second layer 2 from a spool or otherwise may be fed together with the first layer 1 between a first forming member 804 and second forming member 806 in such a way that the first layer 1 and the second layer 2 are in a face to face relationship so that apertures are formed through the first layer 1 and the second layer 2 and side walls of the apertures are coated with the treatment.

The treatment may have a HLB value not higher than about 13.

By treating the apertures with treatment with a HLB value not higher than about 13 which results in areas such as peripheries and sidewalls of the apertures being coated with the treatment, the coated areas become hydrophobic or less hydrophilic than the non-aperture area of the first surface of the first layer. The fluid is less likely to be absorbed by fibers or trapped between fibers in these areas which can lead to reduction of fluid rewet and a stain size. On the other hand, the non-aperture area remains hydrophilic, and negative impact on acquisition speed is minimized.

Therefore, the topsheet as disclosed herein can provides a reduced rewet and clear surface onto the wearer-facing surface of the absorbent article without compromising fast liquid acquisition.

Measurement
1. Contact Angle Test

Figure 10:
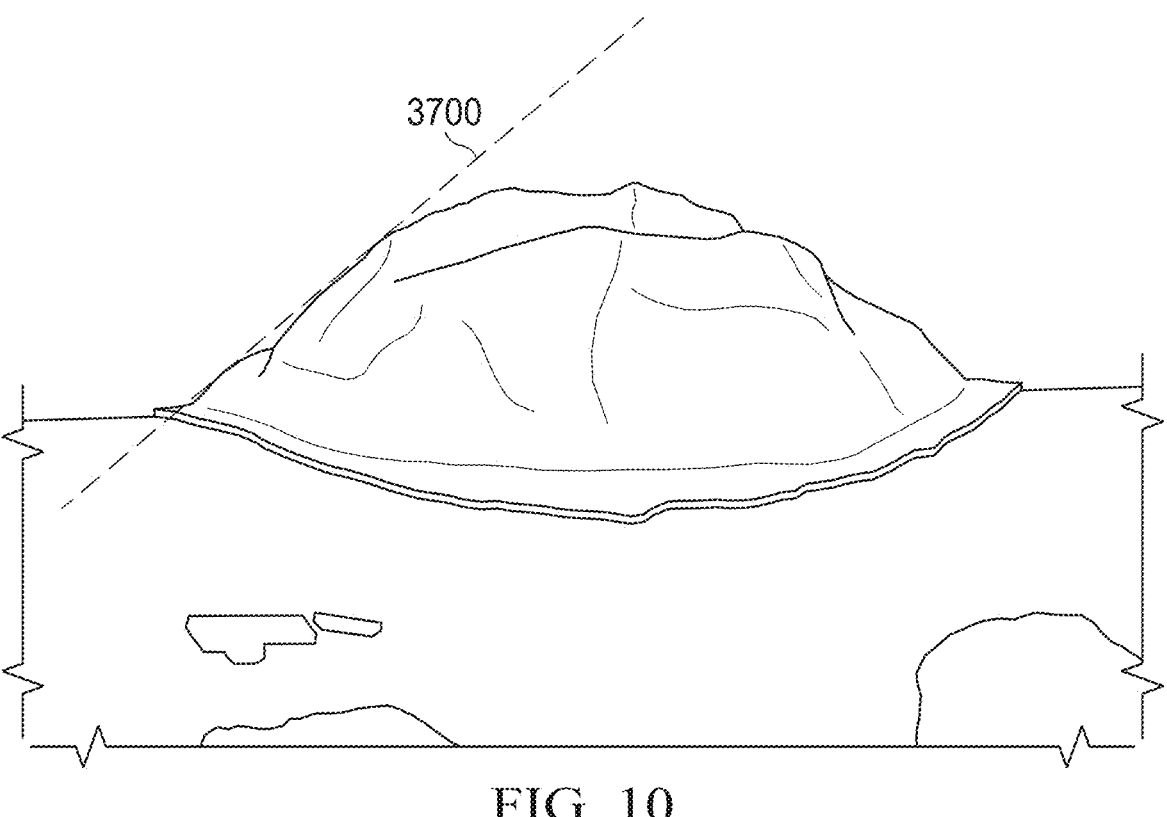
FIG. 10 is a photomicrograph depicting exemplary water droplet on fibers for the contact angle test method disclosed herein.

A rectangular specimen measuring 1 cm×2 cm is cut from a law material nonwoven or a topsheet of a disposable absorbent product taking care not to touch the surface of the specimen or to disturb the structure of the material. The specimen has a length of (2 cm) aligned with a longitudinal centerline of the article. The specimen is handled gently by the edges using forceps and is mounted flat with the skin-facing side up on an SEM specimen holder using double-sided tape and secured with carbon cement. The specimen is sprayed with a fine mist of water droplets generated using a small hobby air-brush apparatus. The water used to generate the droplets is distilled deionized water with a resistivity of at least 18 MΩ-cm. The airbrush is adjusted so that the droplets each have a volume of about 2 pL. Approximately 0.5 mg of water droplets are evenly and gently deposited onto the specimen. Immediately after applying the water droplets, the mounted specimen is frozen by plunging it into liquid nitrogen. After freezing, the sample is transferred to a Quorum PP3010T Cryo-SEM prep chamber at −150° C., coated with Pt, and transferred into Hitachi Ethos NX5000 Cryo-SEM chamber at −150° C. The Hitachi Ethos NX5000 Cryo-SEM or equivalent instrument is used to obtain high-resolution images of the droplets on the fibers. Droplets are randomly selected, though a droplet is suitable to be imaged only if it is oriented in the microscope such that the projection of the droplet extending from the fiber surface is approximately maximized. The contact angle between the droplet and the fiber is determined directly from the image taken as is shown via lines 3700 in FIG. 10.

Such method is performed on the non-aperture area of the first surface of the first layer to measure the first non-aperture area contact angle. Ten separate droplets, located on the non-aperture area in the middle between two neighboring apertures, are imaged from which twenty contact angle measurements are performed (one on each side of each imaged droplet), and the arithmetic average of these twenty contact angle measurements is calculated and reported as the first non-aperture area contact angle.

Such method is also performed on the apertures to measure the aperture contact angle. Ten separate droplets, located near the top of three separate apertures, and ten droplets, located near the bottom of the same three separate apertures, are imaged from which forty contact angle measurements are performed (one on each side of each imaged droplet), and the arithmetic average of these forty contact angle measurements is calculated and reported as the aperture contact angle.

2. Artificial Menstrual Fluid ("AMF") Preparation

AMF is composed of a mixture of defibrinated sheep blood, a phosphate buffered saline solution and a mucous component, and has a viscosity between 7.15 cSt to 8.65 cSt at 23±1° C.

Viscosity on the AMF is performed using a low viscosity rotary viscometer such as Cannon LV-2020 Rotary Viscometer with UL adapter (Cannon Instrument Co., State College, US) or equivalent. The appropriate size spindle for the viscosity range is selected, and instrument is operated and calibrated as per the manufacturer. Measurements are taken at 23±1° C. and at 60 rpm. Results are reported to the nearest 0.01 cSt.

Defibrinated Sheep Blood

Defibrinated sheep blood with a packed cell volume of 38% or greater collected under sterile conditions (available from Cleveland Scientific, Inc., Bath, OH, US) or equivalent is used.

Phosphate Buffered Saline Solution

The phosphate buffered saline solution consists of two individually prepared solutions (Solution A and Solution B). To prepare 1 L of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 L of Solution B, add 1.42±0.005 g of sodium phosphate dibasic anhydrous and 8.50±0.005 g of sodium chloride to a 1000 mL volumetric flask and add distilled water to volume. Mix thoroughly. Add 450±10 mL of Solution B to a 1000 mL beaker and stir at low speed on a stir plate. Insert a calibrated pH probe (accurate to 0.1) into the beaker of Solution B and add enough Solution A, while stirring, to bring the pH to 7.2±0.1.

Mucous Component

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. A successful range of gastric mucin is usually between 38 to 50 grams. To prepare about 500 mL of the mucous component, add 460±10 mL of the previously prepared phosphate buffered saline solution and 7.5±0.5 mL of the 10% w/v potassium hydroxide aqueous solution to a 1000 mL heavy duty glass beaker. Place this beaker onto a stirring hot plate and while stirring, bring the temperature to 45° C.±5° C. Weigh the pre-determined amount of gastric mucin (± 0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range, then remove the beaker from the hot plate and cool to below 40° C. Next add 1.8±0.2 mL of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1° C.

Allow the temperature of the sheep blood and mucous component to come to 23° C.±1° C. Using a 500 mL graduated cylinder, measure the volume of the entire batch of the mucous component and add it to a 1200 mL beaker. Add an equal volume of sheep blood to the beaker and mix thoroughly. Using the viscosity method previously described, ensure the viscosity of the AMF is between 7.15-8.65 cSt. If not, the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1° C. Any unused portion is discarded after testing is complete.

3. Rewet Test

Rewet is measured for an absorbent article loaded with Artificial Menstrual Fluid ("AMF") as described herein.

The fluid amounts left on a topsheet, i.e. rewet under pressure of 0.1 psi are measured after 3.0 ml, 6.0 ml and 9.0 ml AMF are dispensed. All measurements are performed in a laboratory maintained at 23° C.±2° C. and 50%±2% relative humidity.

Test products are removed from all packaging using care not to press down or pull on the products while handling. No attempt is made to smooth out wrinkles. The test products are conditioned at 23° C.±2° C. and 50%±2% relative humidity for at least 2 hours prior to testing.

Place the test product onto a flat, horizontal surface with the body side facing up and load a strikethrough plate on the center of the test product to apply a pressure of 0.25 psi on the test product.

Referring to FIGS. 9A-9E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 9004 6 mm apart. The lateral sides of the reservoir bow outward at a radius 9012 of 14 mm bounded by the overall width, W, of Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm$^2$) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003.

Use a pipette to carefully dispense 3.0 ml of AMF through the open hole of the strikethrough plate onto the center of the test articles within 2 seconds. Once the gush fluid is acquired, remove the plate and start the timer for 3 minutes. After removing the plate, quicky acquire an image of a topsheet of the test product using a color scanner HP Scanjet G4010 or equivalent, and clean the scanner surface after each scan. The image can be analyzed to measure a stain size on a topsheet under Stain Size Test described below. At the end of 3 minutes, place 5 pieces of filter paper (a typical lab filter paper, for example, Ahlstrom #632 12.7 cm×12.7 cm filter papers) that are pre-weighed (termed as "dry weight") are placed on top of an approximate center of an area stained with the fluid. Apply the required mass to generate 0.1 psi pressure on the top of the test product, and keep it under pressure for 5 seconds. Weigh the filter papers again (termed as "wet weight"). The difference between the wet weight and dry weight of the filter paper is the light pressure rewet at the added amount of fluid.

Repeat the step above till total 9.0 ml of fluid is dispensed on the test product. Report the rewet values to the nearest 0.001 gram for the gush level of 3.0 ml, 6.0 ml and 9.0 ml.

In like fashion, a total of three replicate samples are tested for each test product to be evaluated. Report the light pressure rewet as the arithmetic mean of the replicates to the nearest gram.

4. Stain Size Test

The area of a stain visible on a topsheet of an absorbent article due to the fluid left on the topsheet is measured on topsheet images of test products acquired in Rewet Test above for the gush level of 3.0 ml, 6.0 ml and 9.0 ml.

Image analysis is performed using image analysis program such as Image J software (version 1.52p or above, National Institute of Health, USA) or equivalent. The image needs to be distance calibrated with an image of a ruler to give an image resolution, i.e. 7.95 pixels per mm.

Open a topsheet image in Image J. Set the scale according to the image resolution. Crop the image in the center area to make a minimum bounding rectangular selection around the total stain region visible across multiple pad layers. Convert the image type to 8 bit. Apply a Gaussian blur filter to smooth the image by a Gaussian function with a Sigma (radius) of 2. The filtered 8-bit grayscale image is then converted to a binary image using the "Minimum" thresholding method to find the boundary of the stain region on the topsheet (as a result of fluid left on the topsheet) against the lighter-colored stain region from the subsequent layers.

The area of the selected stain region on the topsheet is obtained and recorded as topsheet Stain Size to the nearest 0.01 cm$^2$. This entire procedure is repeated on three substantially similar replicate articles. The reported value is the average of the three individual recorded measurements for topsheet Stain Size to the nearest 0.01 cm$^2$.

Acquisition Time Test

Acquisition time is measured for an absorbent article loaded with AMF as described herein, using a strikethrough plate and an electronic circuit interval timer. The time required for the absorbent article to acquire a dose of AMF is recorded. All measurements are performed in a laboratory maintained at 23° C.±2° C. and 50%±2% relative humidity.

Referring to FIGS. 9A-9E, the strikethrough plate 9001 is constructed of Plexiglas with an overall dimension of 10.2 cm long by 10.2 cm wide by 3.2 cm tall. A longitudinal channel 9007 running the length of the plate is 13 mm deep and 28 mm wide at the top plane of the plate, with lateral walls that slope downward at 65° to a 15 mm wide base. A central test fluid well 9009 is 26 mm long, 24 mm deep and 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length ("L") of 25 mm, width ("W") of 15 mm, and depth ("D") of 8 mm. The longitudinal legs of the reservoir are 4 mm wide and have rounded ends with a radius 9010 of 2 mm. The legs are 3.5 mm apart. The central strut has a radius 9011 of 3 mm and houses the opposing electrodes 9004 6 mm apart. The lateral sides of the reservoir bow outward at a radius 9012 of 14 mm bounded by the overall width, W, of Two wells 9002 (80.5 mm long×24.5 mm wide×25 mm deep) located outboard of the lateral channel, are filled with lead shot to adjust the overall mass of the plate to provide a constraining pressure of 0.25 psi (17.6 gf/cm$^2$) to the test area. Electrodes 9004 are embedded in the plate 9001, connecting the exterior banana jacks 9006 to the inside wall of the fluid reservoir 9003. A circuit interval timer is plugged into the jacks 9006 to the inside wall 9005 of the fluid reservoir 9003. A circuit interval timer (not shown in the drawings) is plugged into the jacks 9006, and monitors the impedance between the two electrodes 9004, and measures the time from introduction of the AMF into reservoir 9003 until the AMF drains from the reservoir. The timer has a resolution of 0.01 sec.

Test products are removed from all packaging using care not to press down or pull on the products while handling. No attempt is made to smooth out wrinkles. The test samples are conditioned at 23° C.±2° C. and 50%±2% relative humidity for at least 2 hours prior to testing.

The required mass of the strikethrough plate must be calculated for the specific dimensions of the test article such that a confining pressure of 1.72 kPa is applied. Determine the longitudinal and lateral midpoint of the article's absorbent core. Measure and record the lateral width of the core to the nearest 0.1 cm. The required mass of the strikethrough plate is calculated as the core width multiplied by strikethrough plate length (10.2 cm) multiplied by 17.6 gf/cm$^2$ and recorded to the nearest 0.1 g. Add lead shot to the plate to achieve the calculated mass.

Connect the electronic circuit interval timer to the strikethrough plate 9001 and zero the timer. Place the test product onto a flat, horizontal surface with the body side facing up. Gently place the strikethrough plate 9001 onto the center of the test product ensuring that the "H" shaped reservoir 9003 is centered over the test area.

Using a mechanical pipette, accurately pipette 3.00 mL±0.05 mL of AMF into the test fluid reservoir 9003. The fluid is dispensed, without splashing, along the molded lip of the bottom of the reservoir 9003 within a period of 3 seconds or less. After the fluid has been acquired, record the acquisition time to the nearest 0.01 second. Thoroughly clean the electrodes 9004 before each test.

In like fashion, a total of three replicate samples are tested for each test product to be evaluated. Report the Acquisition Time (sec) as the mean of the replicates to the nearest 0.01 sec.

6. Non-Aperture Area Size Measurement (A) Sample Preparation

When a nonwoven is available in a raw material form, a specimen with a size of 55 mm×55 mm is cut from the raw material. When a nonwoven is a component of a finished product, the nonwoven is removed from the finished product using a razor blade to excise the nonwoven from other components of the finished product to provide a nonwoven specimen with a size of 55 mm×55 mm A cryogenic spray (such as Cyto-Freeze, Control Company, Houston TX) may be used to remove the nonwoven specimen from other components of the finished product, if necessary.

(B) Image Generation

The nonwoven specimen is placed flat against a dark background under uniform surface lighting conditions. The entire area of the specimen is scanned using an optical microscope such as Keyence 3D Measurement System VR-3200 or equivalent. The analysis such as area ratio measurement is performed using image analysis program such as ImageJ software (version 1.52p or above, National Institutes of Health, USA) and equivalent. The images need to be distance calibrated with an image of a ruler to give an image resolution. Set the scale according to the image resolution and select the field of view size of 55 mm×55 mm for the nonwoven specimen.

(C) Image Analysis—Make a Binary Image

Open a specimen image in ImageJ. Convert the image type to 8 bits. The 8-bit grayscale image is then converted to a binary image (with "black" foreground pixels corresponding to the apertures) using the "Minimum" thresholding method: If the histogram of gray level (GL) values (ranging from 0 to 255, one bin with propensity $P_i$ per gray level i) has exactly two local maxima, the threshold gray level value t is defined as that value for which $P_{t-1} > P_t$ and $P_t \leq P_{t+1}$. If the histogram has greater than two local maxima, the histogram is iteratively smoothed using a windowed arithmetic mean of size 3, and this smoothing is performed iteratively until exactly two local maxima exist. The threshold gray level value t is defined as that value for which $P_{t-1} > P_t$ and $P_t \leq P_{t+1}$. This procedure identifies the gray level (GL) value for the minimum population located between the dark pixel peak of apertures and the lighter pixel peak of the specimen material. If the histogram contains either zero or one local maximum, the method cannot proceed further, and no output parameters are defined.

(D) Size of Non-Aperture Area

Create a filtered image by removing small openings or defects in the binary image using an outlier removing median filter, which replaces a pixel with median of the surrounding area of e.g. 5 pixels in radius if the pixel is darker than the surrounding. Create a reversed image so that discreate non-aperture areas have pixel values of 255.

An ImageJ plugin "Local Thickness" is applied to the image. The local thickness analysis measures the diameter of the largest sphere that fits inside the object and contains the point for each point, i.e., foreground pixel in an image. (reference: "New algorithms for Euclidean distance transformation on an n-dimensional digitized picture with applications", T. Saito and J. Toriwaki, Pattern Recognition 27, 1994, 1551-1565). Convert the image type of local thickness map to 16 bits.

An ImageJ plugin "k-means Clustering" is applied to the image obtained above, which segments the image in the defined number of clusters with similar intensity. The options for k-means clustering used in this analysis are: 5 clusters (i.e., 5 segments image will be divided into); cluster center tolerance of 0.0001; enable randomization seed (randomization seed: 48); show clusters as centroid value. Use the image of clusters represented by centroid value and segment it via centroid value thresholding to only select the discrete non-aperture areas. The histogram data of the binary image is used to calculate the area ratio (%) of discrete non-aperture areas by dividing the counts of foreground pixels (corresponding to the discrete non-aperture areas) with the total pixel counts of the entire area of the image, and multiplying it by 100%. The value is reported to the nearest 1%. The same image is also used for the size/area analysis. Set the scale according to the image resolution. Use watershed segmentation if necessary to separate the discrete non-aperture areas that touch each other. Measure the area $(mm^2)$ of each of the discrete non-aperture areas, when excluding the incomplete ones on the edge of the image. The size/area of discrete non-aperture areas is the arithmetic mean of the area values and reported to the nearest 1 $mm^2$.

EXAMPLES

Example 1: Nonwoven Substrate Preparation

Figure 11:
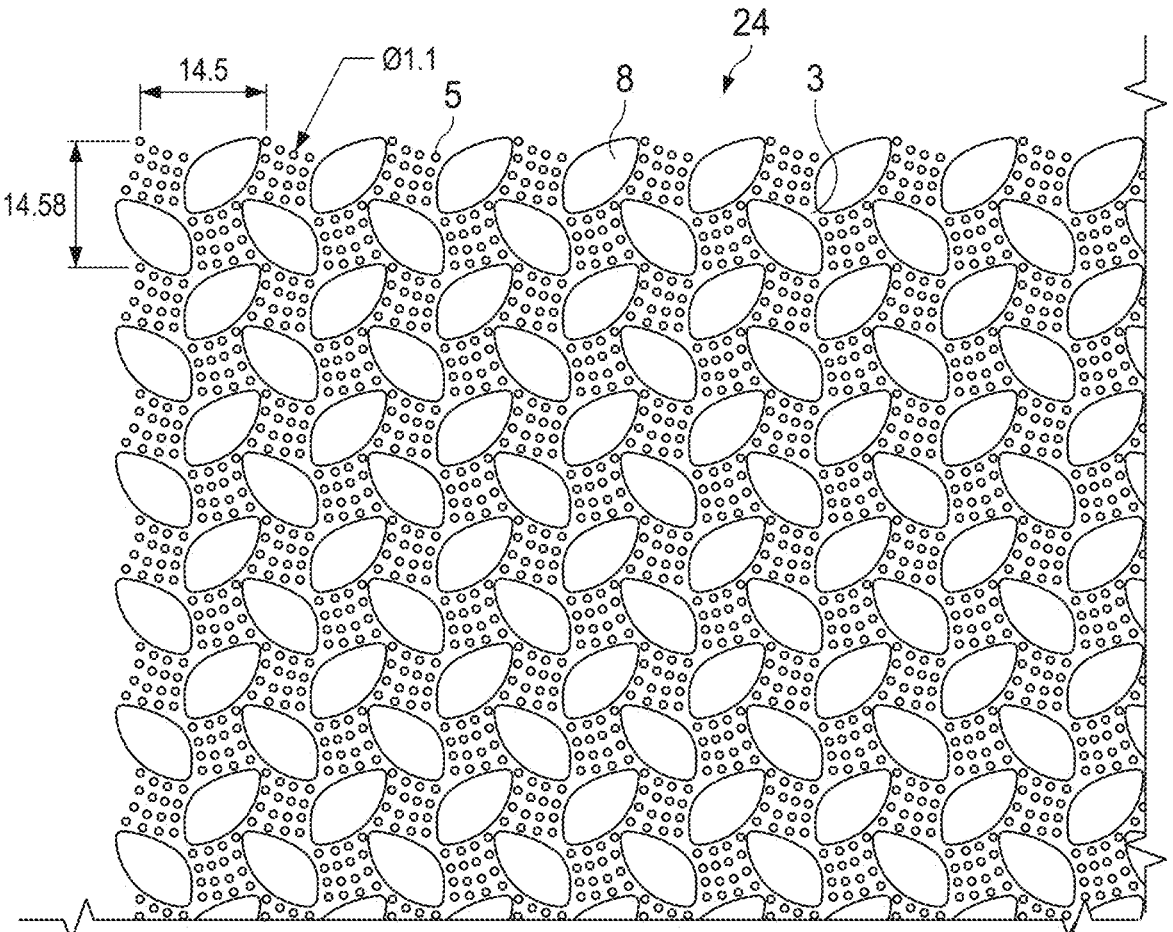
FIG. 11 is a schematic plan view of a topsheet rate disclosed herein.

Using 35 gsm 100% hydrophilic cotton spunlace nonwoven (Xiamen Yanjan New Material Co., Ltd., China) as a first layer and 30 gsm carded air-through nonwoven made by 4D hydrophilic PE/PET fibers as a second layer, various apertured nonwoven substrates were prepared as shown in Table 1 below. All nonwoven substrates were apertured to form apertures in a pattern shown in FIG. 11. The pattern in FIG. 11 has apertures 5, non-aperture area 8 when seen from a first surface 3 of the first layer. It has area non-aperture area size about 78 $mm^2$ measured according to Size of Non-Aperture Area Measurement.

The nonwoven has a first surface 3, a plurality of apertures 5, a plurality of discrete non-aperture areas, and areas 8 in this case. Aperturing of Substrates 1 and 3 were carried out to coat apertures with beeswax emulsion (FX-211, Xiamen Bangdeli Chemical Science & Technology Co. Ltd., China) simultaneously with formation of the apertures.

TABLE 1

|  | Substrate 1 | Substrate 2 | Substrate 3 | Substrate 4 |
|---|---|---|---|---|
| 1st layer | 35 gsm hydrophilic cotton | 35 gsm hydrophilic cotton | 35 gsm hydrophilic cotton | 35 gsm hydrophilic cotton |
| 2nd layer | — | — | 30 gsm carded air-through nonwoven | 30 gsm carded air-through nonwoven |
| Aperture coating material | Beeswax | None | Beeswax | None |

Example 2: Nonwoven Characteristics

A contact angle of a non-aperture area in the first surface of the first layer ("first non-aperture area contact angle") and a contact angle of side walls of apertures ("aperture contact angle") in each nonwoven substrate prepared in Example 1 were measured according to Contact Angle Test disclosed herein. Table 2 below includes measurement results.

TABLE 2

|  | Substrate 1 | Substrate 2 | Substrate 3 | Substrate 4 |
|---|---|---|---|---|
| first non-aperture area contact angle (degree) | 0 | 0 | 0 | 0 |
| aperture contact angle (degree) | 55.5 | 0 | 53.5 | 0 |

Example 3. Absorbent Articles

Sanitary napkins 1-4 as exemplary absorbent articles having topsheets made by nonwoven substrates in Example 1 above were fabricated using a common secondary topsheet, absorbent core and backsheet.

Rewet, a stain size and acquisition speed of each of sanitary napkins 1-4 were measured according to Rewet Test, Stain Size Test, and Acquisition Speed Test disclosed herein. Table 3 below includes the measurement results.

TABLE 3

| Sanitary napkin Topsheet |  | 1 Substrate 1 | 2 Substrate 2 | 3 Substrate 3 | 4 Substrate 4 |
|---|---|---|---|---|---|
| Rewet at 0.1 psi/g | 3 ml | 0.10 | 0.20 | 0.14 | 0.21 |
|  | 6 ml | 0.21 | 0.32 | 0.28 | 0.38 |
|  | 9 ml | 0.34 | 0.43 | 0.44 | 0.50 |
| Stain size $(cm^2)$ | 3 ml | 12.0 | 18.9 | 16.7 | 19.6 |
|  | 6 ml | 22.5 | 33.1 | 28.2 | 34.3 |
|  | 9 ml | 31.2 | 43.9 | 38.7 | 46.5 |
| Acquisition time (sec) | 3 ml | 12.1 | 12.4 | 12.1 | 11.3 |
|  | 6 ml | 36.1 | 36.4 | 39.3 | 34.4 |
|  | 9 ml | 46.3 | 47.6 | 53.0 | 46.7 |

Sanitary napkin 1 having Substrate 1 as a topsheet exhibits a significantly lower rewet and a smaller stain size than Sanitary napkin 2 having Substrate 2 as a topsheet. Sanitary napkin 1, in addition, exhibits acquisition time parity to Sanitary napkin 2.

Sanitary napkin 3 having Substrate 3 as a topsheet exhibits a significantly lower rewet and a smaller stain size than Sanitary napkin 4 having Substrate 4 as a topsheet with a parity fluid acquisition time especially in the first 3 ml gush.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a wearer facing surface and a garment facing surface, the absorbent article comprising a topsheet, a backsheet, and a layer of absorbent material disposed between the topsheet and the backsheet, wherein the topsheet comprises a first layer comprising cellulose-based fibers, the first layer comprising a first surface, an opposite second surface, and a plurality of apertures, wherein the first surface of the first layer forms at least part of the wearer facing surface;

wherein the first surface of the first layer comprises a hydrophilic non-aperture area having a first non-aperture area contact angle as measured by Contact Angle Test; and wherein at least some of the plurality of the apertures have a side wall having an aperture contact angle as measured by Contact Angle Test, the aperture contact angle being higher than the first non-aperture area contact angle; and wherein the first non-aperture area contact angle and the aperture contact angle have a difference of at least about 30°.

2. The absorbent article of claim 1, wherein the aperture contact angle is equal to or higher than about 40° as measured by Contact Angle Test.

3. The absorbent article of claim 1, wherein the first layer further comprises thermoplastic fibers.

4. The absorbent article of claim 1, wherein the non-aperture area does not comprise a treatment.

5. The absorbent article of claim 1, wherein the non-aperture area is treated with a hydrophilic treatment.

6. The absorbent article of claim 1, wherein the side wall of each aperture is coated with a treatment with a HLB value not higher than about 13.

7. The absorbent article of claim 1, wherein the apertures are formed by pin aperturing process.

8. The absorbent article of claim 1, wherein the first layer comprises a plurality of protrusions extending outwardly, away from the absorbent core.

9. The absorbent article of claim 1, wherein the topsheet further comprises a second layer with a first surface, an opposing second surface, a plurality of apertures in such a way that the first surface of the second layer is in a face to face relationship with the second surface of the first layer.

10. The absorbent article of claim 9, wherein the second layer comprises thermoplastic fibers.

11. The absorbent article of claim 9, wherein the second surface of the second layer comprises at least one non-aperture area having a second non-aperture area contact angle, the second non-aperture area contact angle being not greater than the first non-aperture area contact angle.

12. The absorbent article of claim 1, wherein the first layer is a spunlace nonwoven layer.

13. The absorbent article of claim 1, wherein the apertures in the first layer have at least 3% of open area.

14. An absorbent article having a wearer facing surface and a garment facing surface, the absorbent article comprising a topsheet, a backsheet, and a layer of absorbent material disposed between the topsheet and the backsheet, wherein the topsheet comprises a first layer comprising cellulose-based fibers, the first layer comprising a first surface, an opposite second surface, and a plurality of apertures, wherein the first surface of the first layer forms at least part of the wearer facing surface;

wherein the first surface of the first layer comprises a hydrophilic non-aperture area having a first non-aperture area contact angle as measured by Contact Angle Test; and wherein a majority of the apertures have a side wall having an aperture contact angle as measured by Contact Angle Test, the aperture contact angle being higher than the first non-aperture area contact angle; and wherein the first non-aperture area contact angle and the aperture contact angle have a difference of at least about 30°.

15. The absorbent article of claim 14, wherein at least 90% of the apertures have a side wall having an aperture contact angle as measured by Contact Angle Test.

16. An absorbent article having a wearer facing surface and a garment facing surface, the absorbent article comprising a topsheet, a backsheet, and a layer of absorbent material disposed between the topsheet and the backsheet, wherein the topsheet comprises a first layer comprising cellulose-based fibers, the first layer comprising a first surface, an opposite second surface, and a plurality of apertures, wherein the first surface of the first layer forms at least part of the wearer facing surface;

wherein the first surface of the first layer comprises a hydrophilic non-aperture area having a first non-aperture area contact angle as measured by Contact Angle Test; and wherein the first layer within the plurality of apertures is partially interpenetrated into a second layer within the plurality of apertures, and wherein the first layer within the apertures comprises a higher contact angle than the second layer within the apertures;

wherein a majority of the apertures has a side wall having an aperture contact angle as measured by Contact Angle Test, the aperture contact angle being higher than the first non-aperture area contact angle; and wherein the first non-aperture area contact angle and the aperture contact angle have a difference of at least about 30°.

17. The absorbent article of claim 16, wherein the second layer within the plurality of apertures is not completely covered by the first layer within the plurality of apertures.

18. The absorbent article of claim 17, wherein the second layer within the plurality of apertures is exposed in an area proximate to a bottom edge of the apertures.

19. The absorbent article of claim 16, wherein the apertures comprise an open area of from about 2.5% to about 10%.

* * * * *